US007632258B2

(12) United States Patent
Misek et al.

(10) Patent No.: US 7,632,258 B2
(45) Date of Patent: Dec. 15, 2009

(54) MULTILAYER ABSORBENT ARTICLE

(75) Inventors: Jennifer L. Misek, Neenah, WI (US); Danielle G. Finger, Lomira, WI (US); Alice Y. Romans-Hess, Fremont, WI (US); Mary A. Berceau, De Pere, WI (US); Jamie L. Gloede, Oshkosh, WI (US); Candace D. Krautkramer, Neenah, WI (US); Jason M. English, Menasha, WI (US); Jennifer E. Pozniak, Appleton, WI (US); Stuart J. Burgan, Appleton, WI (US); Peter S. Gebhardt, New London, WI (US); Patsy A. Krautkramer, Omro, WI (US); Wendy L. Hamilton, Neenah, WI (US); Amanda J. Carlson, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1375 days.

(21) Appl. No.: 10/392,116

(22) Filed: Mar. 19, 2003

(65) Prior Publication Data
US 2004/0186448 A1 Sep. 23, 2004

(51) Int. Cl.
A61F 13/15 (2006.01)
(52) U.S. Cl. .................. 604/385.101; 604/385.01; 604/380; 604/378; 604/385.21; 604/371
(58) Field of Classification Search ............ 604/385.01, 604/380, 378, 385.101, 385.21, 385.17, 371
See application file for complete search history.

(56) References Cited
U.S. PATENT DOCUMENTS
4,673,402 A * 6/1987 Weisman et al. ............ 604/368
4,699,619 A * 10/1987 Bernardin .................... 604/378

(Continued)

FOREIGN PATENT DOCUMENTS
EP 0 494 112 A 7/1992

(Continued)

OTHER PUBLICATIONS
American Society for Testing Materials (ASTM) Designation: D 1388-96, "Standard Test Method for Stiffness of Fabrics," pp. 313-318, published Jun. 1996.

(Continued)

Primary Examiner—Jackie Stephens
(74) Attorney, Agent, or Firm—Paul Yee; Sebastian Pugliese, III

(57) ABSTRACT

An absorbent feminine care article (20) having a longitudinal direction (22), a lateral direction (24), first and second longitudinally opposed end portions (72, 72a), and an intermediate portion (76) located between the end portions. The article (20) comprises an absorbent body structure (30) sandwiched between a cover (26) and a baffle (28). In a particular aspect, the absorbent structure (30) can include an intake layer (32) and a shaping layer (36). In other aspects, the intake layer (32) and shaping layer (36) can have differently configured absorbent capacities, differently configured densities, differently configured basis weights and/or differently configured sizes which are selectively arranged to provide desired combinations of liquid intake rate, absorbent retention capacity, shape maintenance, and aesthetics.

14 Claims, 11 Drawing Sheets

U.S. PATENT DOCUMENTS

| | | | | |
|---|---|---|---|---|
| 5,549,589 A | * | 8/1996 | Horney et al. | 604/366 |
| 5,607,414 A | * | 3/1997 | Richards et al. | 604/378 |
| 5,858,515 A | | 1/1999 | Stokes et al. | |
| 5,883,231 A | | 3/1999 | Achter et al. | |
| 5,947,945 A | * | 9/1999 | Cree et al. | 604/368 |
| 6,420,626 B1 | * | 7/2002 | Erspamer et al. | 604/378 |

FOREIGN PATENT DOCUMENTS

| | | |
|---|---|---|
| WO | WO 96/40513 A | 12/1996 |
| WO | WO 98/45519 * | 10/1998 |
| WO | WO 98/51250 A1 | 11/1998 |
| WO | WO 00/19955 A2 | 4/2000 |
| WO | WO 00/37011 A | 6/2000 |
| WO | WO 01/26596 A1 | 4/2001 |

OTHER PUBLICATIONS

Fellers, Christer, "Edgewise Compression Strength of Paper," Handbook of Physical and Mechanical Testing of Paper and Paperboard, Marcel Dekker, Inc., New York, vol. 1, 1983, pp. 349-381.

* cited by examiner

_MULTILAYER ABSORBENT ARTICLE_

FIELD OF THE INVENTION

The present invention relates to an absorbent article. More particularly, the present invention pertains to an absorbent system for a feminine care article, such as an absorbent feminine care pad.

BACKGROUND OF THE INVENTION

Absorbent products intended to absorb discharged body fluids are well known in the art. Such absorbent products generally comprise a fibrous mass or other absorbent body which can absorb and hold the body fluids. Similarly, it is well known that feminine care articles have been employed to absorb and hold liquids, such as urine and/or menses. The absorbent articles have included various systems of liquid-handling layers, such as intake layers, distribution layers, retention layers and the like. Additionally, the absorbent articles have included wing portions which can help to hold the article in place at a selected location in a wearer's undergarment. Various fasteners have been employed to secure the wing portions in a desired configuration during ordinary use. The fasteners have included adhesive fasteners as well as mechanical fasteners, and the mechanical fasteners have included conventional, hook-and-loop fasteners.

Conventional absorbent systems, however, have not provided desired combinations of comfort, rapid intake of liquid, low surface staining, low leakage and surface dryness. When such conventional absorbent systems have been constructed to provide desired levels of comfort to the wearer, the liquid-handling properties have been less than desired. As a result, there has been a continued need for improved absorbent systems that provide more secure levels of liquid intake and storage, along with increased levels of comfort.

BRIEF DESCRIPTION OF THE INVENTION

Generally stated, the present invention provides an absorbent article having a longitudinal direction, a lateral direction, first and second longitudinally opposed end portions, and an intermediate portion located between the end portions. The article comprises an absorbent body sandwiched between a cover and a baffle. In a particular aspect, the article can include an absorbent body having an intake layer and a shaping layer. In other aspects, the intake and shaping layers can have different absorbent capacities, different densities, different basis weights and/or different sizes which are selectively configured to provide desired combinations of liquid intake rate, absorbent retention capacity, shape maintenance, and aesthetics.

By incorporating its various features and configurations, the article of the invention can better maintains its shape, provide less bunching or twisting, and provide greater comfort and fit. The article can provide an improved retention of liquid, and can provide more absorbent capacity from the same overall pad shape. Additionally, the article can position faster liquid intake properties in a more centralized, target region of the article where the liquid is more likely to be introduced into the article, and can provide a drier pad surface. Particular features can provide improved aesthetics and visual cues or perceptions of absorbency. The article can be less susceptible to premature leakage, and can provide greater protection and confidence to the wearer.

BRIEF DESCRIPTION OF THE DRAWINGS

The various features, aspects and advantages of the present invention will become better understood with reference to the following description, appended claims and accompanying drawings where:

DETAILED DESCRIPTION OF THE INVENTION

Figure 1:
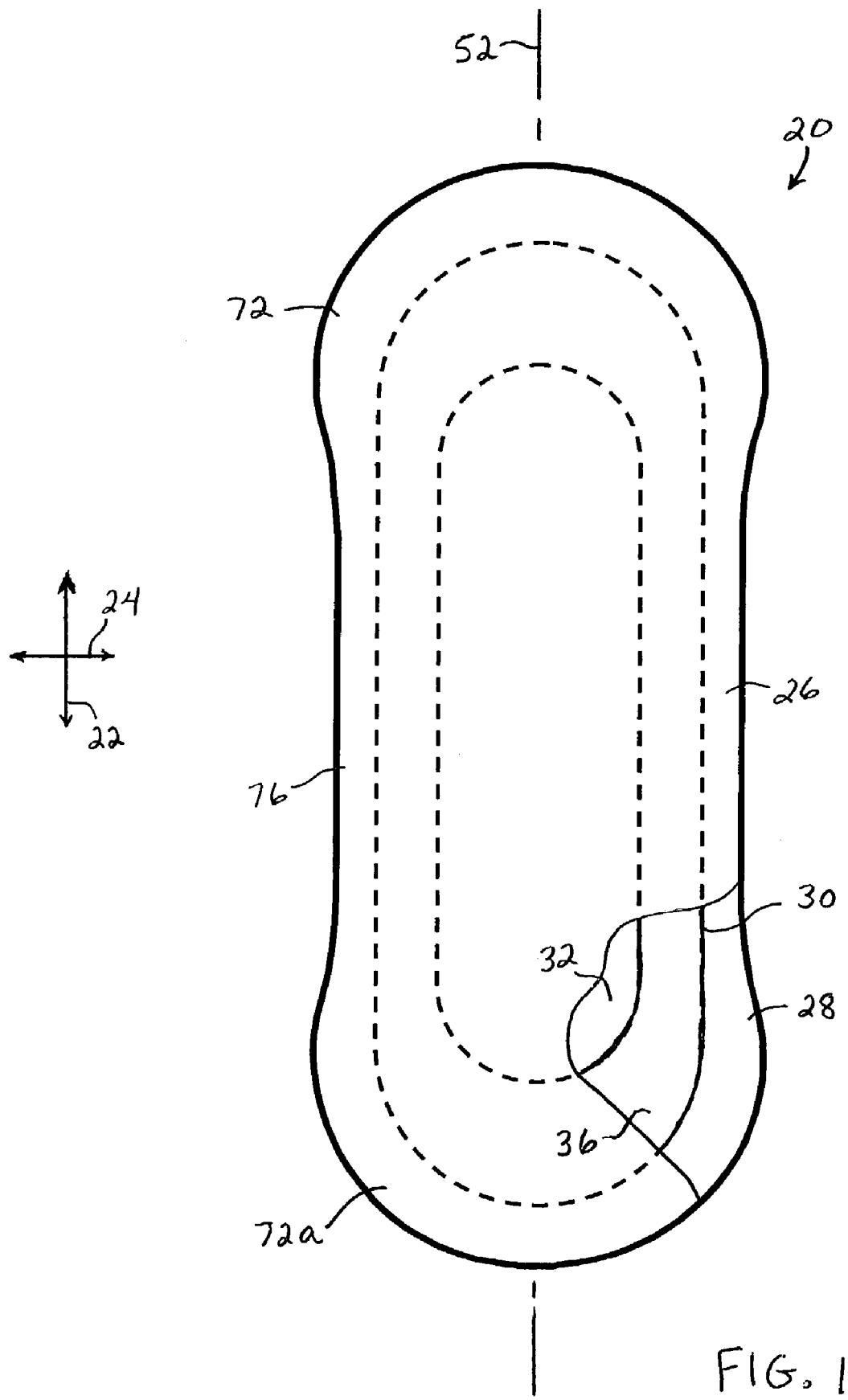
FIG. 1 shows a representative, partially cut-away, top, plan view of a garment-side of an absorbent article in which separately side-panels or wings are assembled to the article and arranged in a storage position.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

By the terms "particle," "particles," "particulate," "particulates" and the like, it is meant that the material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

As used herein, the term "nonwoven" refers to a fabric web that has a structure of individual fibers or filaments which are interlaid, but not in an identifiable repeating manner.

As used herein, the terms "spunbond" or "spunbonded fiber" refer to fibers which are formed by extruding filaments of molten thermoplastic material from a plurality of fine, usually circular, capillaries of a spinneret, and then rapidly reducing the diameter of the extruded filaments.

As used herein, the phrase "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers.

"Coform" as used herein is intended to describe a blend of meltblown fibers and cellulose fibers that is formed by air forming a meltblown polymer material while simultaneously blowing air-suspended cellulose fibers into the stream of meltblown fibers. The meltblown fibers containing wood fibers are collected on a forming surface, such as provided by a foraminous belt. The forming surface may include a gas-pervious material, such as spunbonded fabric material, that has been placed onto the forming surface.

As used herein, the phrase "complex liquid" describes a liquid generally characterized as being a viscoelastic liquid comprising multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water and the like, are generally characterized as being relatively low-viscosity and comprising one or more components having homogeneous physical and/or chemical properties. As a result of having homogeneous properties, the one or more components of simple liquids behave substantially similarly during absorption or adsorption, although some components may be absorbed or adsorbed more readily than others.

Although a complex liquid is generally characterized herein as including specific components having inhomogeneous properties, each specific component of a complex liquid generally has homogeneous properties. Consider for example a representative complex body-liquid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

As used herein, the term "hydrophilic" describes fibers or the surfaces of fibers that are welted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 900 are designated "wettable" or hydrophilic, while fibers having contact angles equal to or greater than to 90° are designated "nonwettable" or hydrophobic. When comparing materials, a material that forms a relatively larger contact angle with water is relatively less hydrophilic than a material that forms a smaller contact angle with water.

As used herein, the phrase "absorbent article" refers to devices which absorb and contain body liquids, and more specifically, refers to devices which are placed against or near the skin to absorb and contain the various liquids discharged from the body. The term "disposable" is used herein to describe absorbent articles that are not intended to be laundered or otherwise restored or reused as an absorbent article after a single use. Examples of such disposable absorbent articles include, but are not limited to: health care related products including surgical drapes, gowns, and sterile wraps; personal care absorbent products such as feminine hygiene products (e.g., sanitary napkins, pantiliners, tampons, interlabial devices and the like), infant diapers, children's training pants, adult incontinence products and the like; as well as absorbent wipes and covering mats.

Disposable absorbent articles'such as, for example, many of the feminine care absorbent products, can include a liquid pervious topsheet, a substantially liquid impervious backsheet joined to the topsheet, and an absorbent core positioned and held between the topsheet and the backsheet. The topsheet is operatively permeable to the liquids that are intended to be held or stored by the absorbent article, and the backsheet may be substantially impermeable or otherwise operatively impermeable to the intended liquids. The absorbent article may also include other components, such as liquid wicking layers, liquid intake layers, liquid distribution layers, transfer layers, barrier layers, and the like, as well as combinations thereof. Disposable absorbent articles and the components thereof can operate to provide a body-facing surface and a garment-facing surface. As used herein, the body-facing or bodyside surface means that surface of the article or component which is intended to be disposed toward or placed adjacent to the body of the wearer during ordinary use, while the outward, outward-facing or garment-side surface is on the opposite side, and is intended to be disposed to face away from the wearer's body during ordinary use. Such outward surface may be arranged to face toward or placed adjacent to the wearer's undergarments when the absorbent article is worn.

Figure 1A:
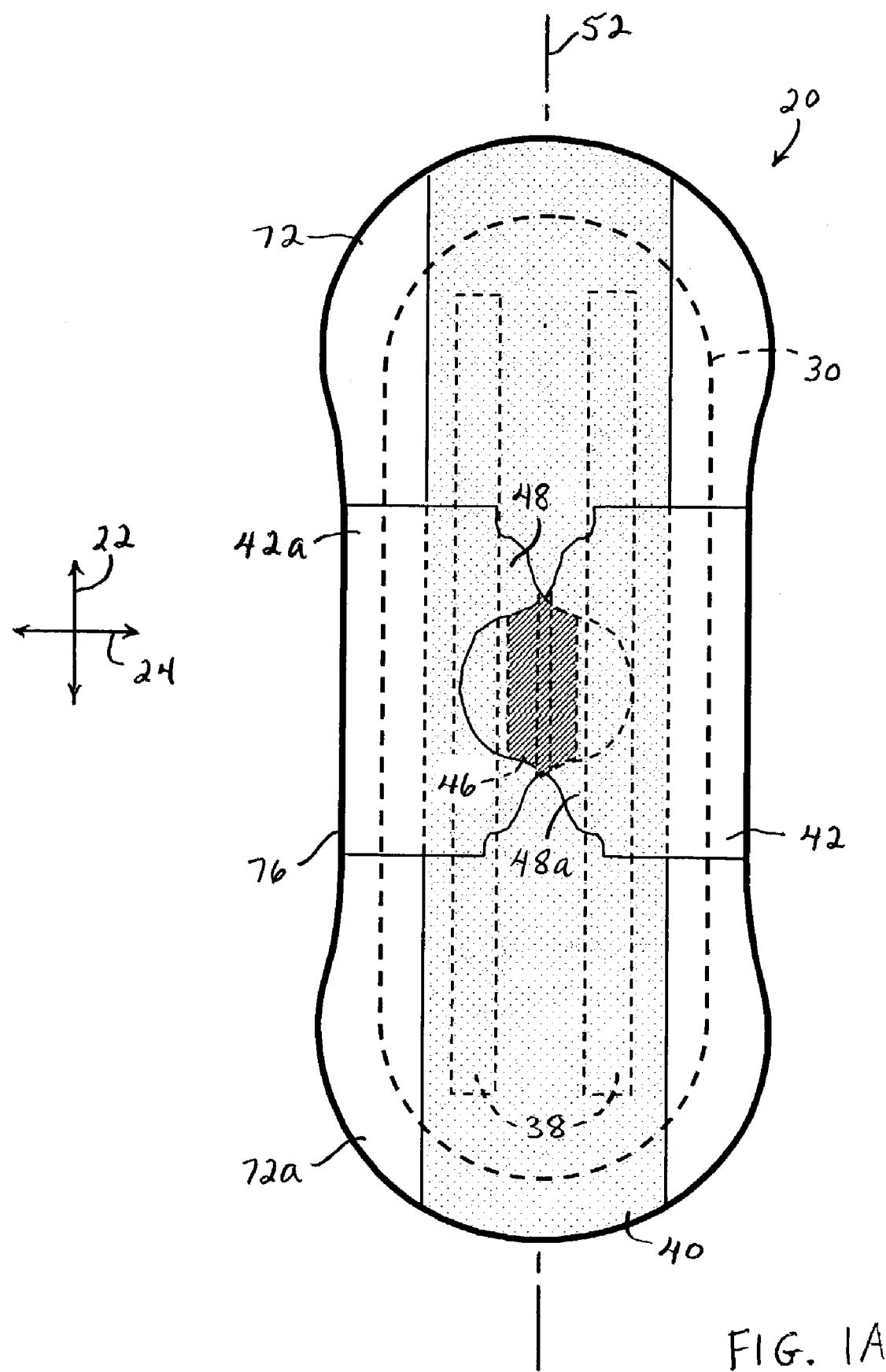
FIG. 1A shows a representative, bottom, plan view of a bodyside of the absorbent article illustrated in FIG. 1.
Figure 1B:
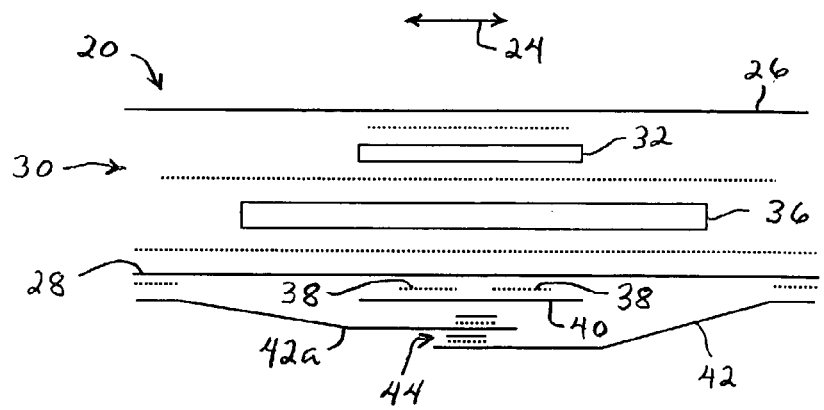
FIG. 1B shows an expanded, schematic view of a representative, transverse cross-section of the absorbent article illustrated in FIG. 1.
Figure 1C:
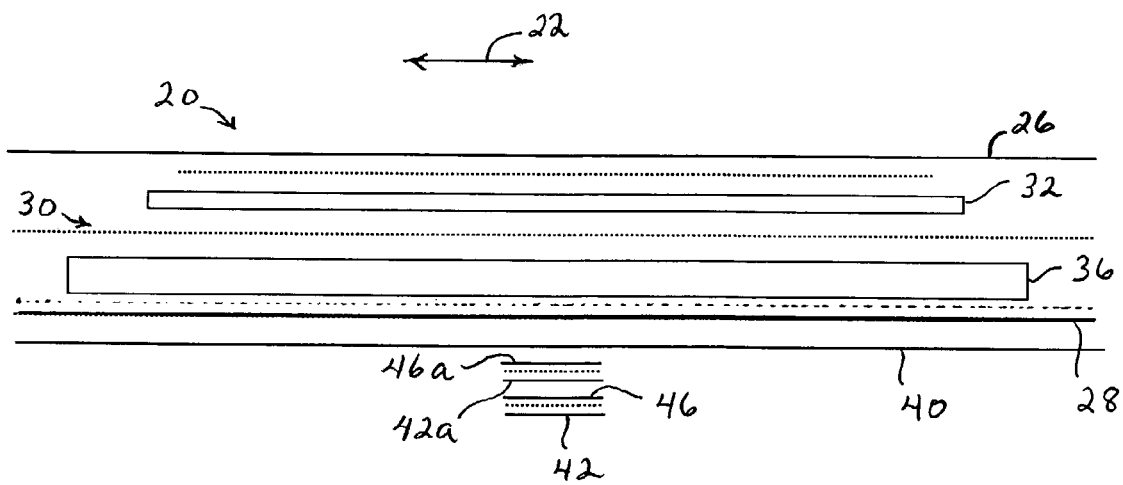
FIG. 1C shows an expanded, schematic view of a representative, longitudinal cross-section of the absorbent article illustrated in FIG. 1.

FIGS. 1 through 1C, illustrate an example of a suitable article, such as the representatively shown feminine care article, which is configured to incorporate the present invention. The feminine care article can, for example, be a feminine care pad or napkin 20, and the article can have a lengthwise longitudinal direction 22, a transverse, laterally extending, cross-direction 24, first and second longitudinally opposed end portions 72 and 72a, and an intermediate portion 76 located between the end portions. As representatively shown, the longitudinal dimension of the article is relatively larger than the lateral dimension of the article. The article 20 can include a topsheet or cover 26, a baffle 28, and an absorbent structure 30 positioned between the cover and baffle. In a particular aspect, the absorbent structure 30 can at least include an intake layer 32 and a shaping layer 36. In other aspects, the intake and shaping layers can have configurations of absorbent capacities, configurations of densities, configurations of basis weights and/or configurations of sizes which are selectively constructed and arranged to provide desired combinations of liquid intake time, absorbent saturation capacity, absorbent retention capacity, z-directional liquid distribution along the thickness dimension of the article, shape maintenance, and aesthetics.

By incorporating its various features, aspects and configurations, alone or in desired combinations, the article of the invention can provide an improved absorbent system that can take better advantage of the functional properties of a distinctive bottom, garment-side layer. The improved absorbent article can better maintain a desired shape (e.g. with less bunching or twisting), and can better maintain a larger surface area for liquid storage and retention. The article can also provide more absorbent capacity without increasing the area that is overlaid by the overall shape of the absorbent structure. Additionally, the article can more efficiently locate materials having faster liquid-intake properties, and position such materials in the center of the absorbent structure where incoming liquid is more likely to be directed. The article can also provide a drier bodyside surface, and in particular configurations, can provide visual cues of absorbency. Desired arrangements can provide improved appearance and aesthetics. As a result, the article of the invention can provide greater comfort and fit, and improved protection and increased confidence.

The cover 26 may include a layer constructed of any operative material, and may be a composite material. For example, the cover layer can include a woven fabric, a nonwoven fabric, a polymer film, a film-fabric laminate or the like, as well as combinations thereof. Examples of a nonwoven fabric include spunbond fabric, meltblown fabric, coform fabric, a carded web, a bonded-carded-web, a bicomponent spunbond fabric or the like as well as combinations thereof. For example, the cover layer can include a woven fabric, a nonwoven fabric, a polymeric film that has been configured to be operatively liquid-permeable, or the like, as well as combinations thereof. Other examples of suitable materials for constructing the cover layer can include rayon, bonded carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof.

A more particular example of a suitable cover layer material can include a bonded-carded-web composed of polypropylene and polyethylene, such as has been used as a cover stock for KOTEX brand pantiliners, and has been obtainable from Vliesstoffwerk Christian Heinrich Sandler GmbH & Co. KG, a business having an address at Postfach 1144, D95120 Schwarzenbach/Saale, Germany. Other examples of suitable materials are composite materials of a polymer and a nonwoven fabric material. The composite materials are typically in the form of integral sheets generally formed by the extrusion of a polymer onto a web of spunbond material. In a desired arrangement, the cover layer 26 can be configured to be operatively liquid-permeable with regard to the liquids that the article is intended to absorb or otherwise handle. The operative liquid-permeability may, for example be provided by a plurality of pores, perforations, apertures or other openings, as well as combinations thereof, that are present or formed in the cover layer. The apertures or other openings can help increase the rate at which bodily liquids can move through the thickness of the cover layer and penetrate into the other components of the article (e.g. into the absorbent structure 30). The selected arrangement of liquid-permeability is desirably present at least on an operative portion of the cover layer that is appointed for placement on the body-side of the article. The cover layer 26 can provide comfort and conformability, and can function to direct bodily exudates away from the body and toward the absorbent structure 30. In a desired feature, the cover layer 26 can be configured to retain little or no liquid in its structure, and can be configured to provide a relatively comfortable and non-irritating surface next to the body-tissues of a female wearer. The cover layer 26 can be constructed of any material which is also easily penetrated by bodily fluids that contact the surface of the cover layer.

The cover 26 can also have at least a portion of its bodyside surface treated with a surfactant to render the cover more hydrophilic. The surfactant can permit arriving bodily liquids to more readily penetrate the cover layer. The surfactant may also diminish the likelihood that the arriving bodily fluids, such as menstrual fluid, will flow off the cover layer rather than penetrate through the cover layer into other components of the article (e.g. into the absorbent body structure). In a particular configuration, the surfactant can be substantially evenly distributed across at least a portion of the upper, bodyside surface of the cover 26 that overlays the upper, bodyside surface of the absorbent.

The cover 26 may be maintained in secured relation with the absorbent structure 30 by bonding all or a portion of the adjacent surfaces to one another. A variety of bonding articles known to one of skill in the art may be utilized to achieve any such secured relation. Examples of such articles include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The cover 26 typically extends over the upper, bodyside surface of the absorbent structure, but can alternatively extend around the article to partially or entirely, surround or enclose the absorbent structure. Alternatively, the cover 26 and the baffle 28 can have peripheral margins which extend outwardly beyond the terminal, peripheral edges of the absorbent structure 30, and the extending margins can be joined together to partially or entirely, surround or enclose the absorbent structure.

The baffle 28 may include a layer constructed of any operative material, and may or may not have a selected level of liquid-permeability or liquid-impermeability, as desired. In a particular configuration, the backsheet or baffle 28 may be configured to provide an operatively liquid-impermeable baffle structure. The baffle may, for example, include a polymeric film, a woven fabric, a nonwoven fabric or the like, as well as combinations or composites thereof. For example, the baffle may include a polymer film laminated to a woven or nonwoven fabric. In a particular feature, the polymer film can be composed of polyethylene, polypropylene, polyester or the like, as well as combinations thereof. Additionally, the polymer film may be micro-embossed, have a printed design, have a printed message to the consumer, and/or may be at least partially colored. Desirably, the baffle 28 can operatively permit a sufficient passage of air and moisture vapor out of the article, particularly out of an absorbent (e.g. storage or absorbent structure 30) while blocking the passage of bodily liquids. An example of a suitable baffle material can include a breathable, microporous film, such as a HANJIN Breathable Baffle available from Hanjin Printing, Hanjin P&C Company Limited, a business having offices located in Sahvon-li.Jungan-mvu.Kongiu-City, Chung cheong nam-do, Republic of South Korea. The baffle material is a breathable film, which is white in color, dimple embossed and contains: 47.78% calcium carbonate, 2.22% $TiO_2$, and 50% polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable baffle material can include a closed cell polyolefin foam. For example, a closed cell polyethylene foam may be employed. Still another example of a baffle material would be a material that is similar to a polyethylene film which is used on commercially sold KOTEX brand pantiliners, and is obtainable from Pliant Corporation, a business having offices located in Schaumburg, Ill., USA.

The structure of the absorbent body 30 can be operatively configured to provide a desired level of absorbency or storage capacity. More particularly, the absorbent body can be configured to hold a liquid, such as urine, menses, other complex liquid or the like, as well as combinations thereof. As representatively shown, the absorbent body can include a matrix of absorbent fibers and/or absorbent particulate material, and the absorbent fiber can include natural and/or synthetic fiber. Additionally, the absorbent body may include one or more components that can modify menses or intermenstrual liquid.

The absorbent structure 30 may also include superabsorbent material. Superabsorbent materials suitable for use in the present invention are known to those skilled in the art, and may be in any operative form, such as particulate form. Generally stated, the superabsorbent material can be a water-swellable, generally water-insoluble, hydrogel-forming polymeric absorbent material, which is capable of absorbing at least about 20, desirably about 30, and possibly about 60 times or more its weight in physiological saline (e.g. saline with 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors such as The Dow Chemical Company and Stockhausen, Inc. The superabsorbent material may desirably be included in an appointed storage or retention portion of the absorbent system, and may optionally be employed in other components or portions of the absorbent article.

In particular configurations, the absorbent body 30 can be included in a feminine care article, and can provide a composite, overall absorbent saturation capacity which is at least a minimum of about 5.5 grams of menses simulant A. The overall absorbent saturation capacity can alternatively be at least about 40 grams of menses simulant A to provide improved performance. In other aspects, the overall absorbent saturation capacity can be up to a maximum of about 120 grams of menses simulant A, or more, and can alternatively be up to about 88 grams of menses simulant A to provide improved effectiveness. In a desired arrangement, the composite, overall absorbent saturation capacity can be about 60 grams of menses simulant A.

In particular configurations, the absorbent body 30 can be included in a feminine care article, and can provide a composite, overall absorbent retention capacity which is at least a minimum of about 5.0 grams of menses simulant A. The overall absorbent retention capacity can alternatively be at least about 10 grams of menses simulant A to provide improved performance. In other aspects, the overall absorbent retention capacity can be up to a maximum of about 34 grams of menses simulant A, or more, and can alternatively be up to about 20 grams of menses simulant A to provide improved effectiveness. In a desired arrangement, the composite, overall absorbent retention capacity can be about 14.5 grams of menses simulant A.

The menses simulant A is composed of swine blood diluted with swine plasma to provide a hematocrit level of 35% (by volume). A suitable device for determining the hematocrit level is a HEMATOSTAT-2 system, available from Separation Technology, Inc., a business having offices located in Altamonte Springs, Fla., U.S.A. A substantially equivalent system may alternatively be employed. Simulant A is typically used for absorbent capacity tests, where the viscoelastic properties that affect liquid movement have been found to be of little importance.

As representatively shown, the absorbent body 30 of the selected article can comprise a composite structure having a selected plurality of strata or layers. With reference to FIGS. 1 through 1C, for example, the absorbent composite can include an intake layer 32 and an absorbent shaping layer 36, as well as any other desired components, arranged in any operative combination. As representatively shown, the structure of the absorbent body can include an absorbent pad, shaping layer 36 which is positioned between the cover 26 and the baffle 28, and can include an intake layer 32 which is positioned between the cover 26 and the shaping layer 36.

In a particular aspect, the article 20 can include a top, bodyside intake layer 32 which is sized and placed to more effectively operate in a target area of the absorbent body 30 where liquids are more likely to be introduced into the article. The material of the intake layer can be configured to provide desired liquid-intake properties, substantially without consideration for delivering shaping properties. For example, the configuration of the intake layer need not include properties that are configured to prevent bunching and twisting of the article, particularly the absorbent structure, during ordinary wear.

The intake layer can include material that is configured to quickly absorb and pull liquid away from the body. Accordingly, the intake layer 32 can provide the function of liquid intake and can also provide the functions of liquid distribution, spreading, temporary storage and liquid retention. The intake layer may include natural fibers, synthetic fibers, superabsorbent materials, a woven fabric; a nonwoven fabric; a wet-laid fibrous web; a substantially unbonded airlaid fibrous web; an operatively bonded, stabilized-airlaid fibrous web; or the like, as well as combinations thereof. Additionally, the absorbent body may include one or more components that can modify menses or intermenstrual liquid.

In a particular arrangement, the intake layer can be a thermally-bonded, stabilized airlaid fibrous web (e.g. Concert code 175.1020) available from Concert Fabrication, a business having offices located in Gatineaux, Quebec, Canada. The intake layer may optionally be provided by a similar, stabilized airlaid fibrous web available from Buckeye Technologies, Inc., a business having offices located in Memphis, Tenn., U.S.A.

In a desired feature, the intake layer 32 can have a relatively lower basis weight, as compared to the bottom (garment-side) retention/shaping layer 36. Optionally, the basis weight of the intake layer may be equal or similar to the basis weight of the shaping layer. In another feature, the intake layer 32 can have a lower density (e.g., be more lofty), as compared to the retention/shaping layer 36.

In a particular aspect, the basis weight of the intake layer 32 can be at least a minimum of about 30 g/m². The basis weight of the intake layer can alternatively be at least about 100 g/m², and can optionally be at least about 120 g/m² to provide improved performance. In other aspects, the basis weight of the intake layer can be up to a maximum of about 250 g/m², or more. The basis weight of the intake layer can alternatively be up to about 200 g/m², and can optionally be up to about 175 g/m² to provide improved effectiveness.

If the basis weight of the intake layer 32 is outside the desired values, the article can be too thick and bulky, and can provide poor comfort and excessive awareness of the article during use. An overly high basis weight can excessively decrease the amount of liquid transferred to the shaping layer 36, can undesirably increase the amount of liquid held in the intake layer and/or can be excessively expensive. An overly low basis weight can excessively limit the ability to acquire, temporarily store and transfer liquid, and can permit premature leakage. If the basis weight of the intake layer is outside the desired values, the article can also exhibit an excessively high rewet or flowback to the wearer's skin and provide an undesired wet, moist feel to the wearer. Additionally, the intake layer can present an excessively low void volume to subsequent inputs of liquid, and the low void volume can contribute to premature leakage and excessive rewet or flowback to the wearer's skin.

In another aspect, the density of the intake layer 32 can be at least a minimum of about 0.01 g/cm³. The intake layer density can alternatively be at least about 0.02 g/cm³, and can optionally be at least about 0.04 g/cm³ to provide improved performance. In still other aspects, the intake layer density can be up to a maximum of about 0.1 g/cm³, or more. The intake layer density can alternatively be up to about 0.09 g/cm³, and can optionally be up to about 0.08 g/cm³ to provide improved effectiveness. In a desired arrangement, the density of the intake layer can be about 0.06 g/cm³.

If the density of the intake layer 32 is outside the desired values, the article can exhibit excessive leakage, and can provide an undesired moist, wet feeling against the wearer's skin. An overly high density can limit the saturation capacity of the intake layer and can provide excessively low permeability. This can excessively slow the acquisition and intake of liquid. Additionally, an overly high density can decrease and inhibit the desired liquid transfer to the lower, shaping layer 36. Insufficient liquid transfer can increase rewet or flowback of liquid to the wearer's skin and can decrease the void volume in the intake layer that is available to absorb a follow-up input of liquid, resulting in an increased likelihood of a premature leak. An overly low density can provide an excessively low web tensile strength, and can cause web handling problems. Depending on the basis weight, a low density can provide an excessively thick bulky intake layer that can cause poor comfort and excessive awareness of the product. A low intake layer density can also allow discrete amounts of liquid to be immobilized within the intake structure. This liquid can then be available to increase the likelihood of liquid rewet and flowback to the wearer's skin. Additionally, an overly low density intake structure can provide excessively high permeability. As a result, the properties of liquid control, spreading, distribution and temporary storage can be inadequate. The article can also allow premature leakage or an undesirably moist, wet skin.

A further feature of the intake layer 32 can be its total absorbent saturation capacity. In particular aspects, the intake layer saturation capacity can be at least a minimum of about 0.5 grams of menses simulant A (0.5 g). The intake layer saturation capacity can alternatively be at least about 5 grams of menses simulant A, and can optionally be at least about 10 grams of menses simulant A to provide improved performance. In other aspects, the intake layer, total saturation capacity can be up to a maximum of about 20 grams of menses simulant A, or more. The intake layer saturation capacity can alternatively be up to about 19 grams of menses simulant A, and can optionally be up to about 18 grams of menses simulant A to provide improved effectiveness. In a desired arrangement, the total saturation capacity of the intake layer can be about 14 grams of menses simulant A.

In another feature, the intake layer 32 can have a distinctive total absorbent retention capacity. The intake layer retention capacity can be at least a minimum of about 0.3 grams of menses simulant A (0.3 g). The intake layer retention capacity can alternatively be at least about 1 gram of menses simulant A, and can optionally be at least about 1.8 grams of menses simulant A to provide improved performance. In other aspects, the intake layer, total retention capacity can be up to a maximum of about 3.8 grams of menses simulant A, or more. The intake layer retention capacity can alternatively be up to about 3 grams of menses simulant A, and can optionally be up to about 2.4 grams of menses simulant A to provide improved effectiveness. In a desired arrangement, the total retention capacity of the intake layer can be about 2.1 grams of menses simulant A.

A particular feature of the intake layer 32 can include a specific, absorbent saturation capacity. In particular aspects, specific saturation capacity of the intake layer can be at least a minimum of about 9 grams of menses simulant A per gram of intake layer material (9 g/g), or at least about 10 g/g. The specific saturation capacity can alternatively be at least about 10.5 g/g, and can optionally be at least about 11 g/g to provide improved performance. In other aspects, the intake layer, specific saturation capacity can be up to a maximum of about 15 g/g, or more. The specific saturation capacity can alternatively be up to about 14.5 g/g, and can optionally be up to about 14 g/g to provide improved effectiveness. In a desired arrangement, the specific saturation capacity of the intake layer can be about 13 g/g.

In still another feature, the intake layer 32 can include a specific, absorbent retention capacity. In particular aspects, the intake layer, specific retention capacity can be at least a minimum of about 1.5 grams of menses simulant A per gram of intake layer material (1.5 g/g). The specific retention capacity can alternatively be at least about 1.6 g/g, and can optionally be at least about 1.7 g/g to provide improved performance. In other aspects, the specific retention capacity of the intake layer 32 can be up to a maximum of about 2.5 g/g, or more. The specific retention capacity can alternatively be up to about 2.4 g/g, and can optionally be up to about 2.3 g/g to provide improved effectiveness. In a desired arrangement, the specific retention capacity of the intake layer can be about 2 g/g.

A particular feature can include an intake layer 32 which includes fibers that can provide an intake layer that is relatively more "hydrophilic" than the shaping layer 36. Still another feature can include an intake layer wherein at least an operative portion of the fibers have been semi-treated by incorporating a debonding agent to improve opening and fiberization during the manufacturing process.

Additionally, the intake layer can be configured to exhibit a distinctive stiffness value. In a particular feature the stiffness value of the intake layer can be at least a minimum of about 5.5 cm, as determined by a cantilever bending test. In a further feature, the stiffness value can be not more than a maximum of about 7 cm. A suitable cantilever bending test is ASTM Standard Test D 1388, with the following modification: The size of the test specimen is 1 inch×8 inch. The longer specimen allows greater accuracy when testing stiffer fabrics, since it is desirable to avoid data readings in the last inch of specimen length.

Another feature can include a top, bodyside intake layer 32 having an area size which is relatively smaller than an area size of the bottom, garment-side shaping layer 36. Additionally, the area of the intake layer 32 can be a distinctive percentage of the area of the shaping layer 36. It should be readily appreciated that the area of a component can be determined from its longitudinal length, lateral width, and shape. In a particular aspect the intake layer area percentage can be at least a minimum of about 20% or 25%. The intake layer area percentage can alternatively be at least about 30% or 35%, and can optionally be at least about 40% or 45% to provide improved performance. In other aspects, the intake layer area percentage can be up to a maximum of about 80% or 85%. The intake layer area percentage can alternatively be up to about 75%, and can optionally be up to about 55% or 60% to provide improved effectiveness. In desired arrangements, the intake layer 32 might have a surface area that is approximately 45-50% of the surface area of the shaping layer 36.

In a particular aspect, the intake layer 32 can have a longitudinal length which spans at least a minimum of about 15% or 20% of a total, longitudinal length of the shaping layer 36. The intake-layer length can alternatively be at least about 46% of the total, longitudinal length of the shaping layer 36, and can optionally be at least about 75% or 80% of the total, longitudinal length of the shaping layer to provide improved performance. In other aspects, the intake-layer length can be up to a maximum of about 95% of the total, longitudinal length of the shaping layer 36. The intake-layer length can alternatively be up to about 90% of the total, longitudinal length of the shaping layer, and can optionally be up to about 85% of the total, longitudinal length of the shaping layer to provide improved effectiveness.

In another aspect, the intake layer 32 can have a cross-directional, lateral width which spans at least a minimum of about 25% of a total, lateral width of the shaping layer 36. The intake-layer width can alternatively be at least about 40% of the total, lateral width of the shaping layer 36, and can optionally be at least about 58% of the total, lateral width of the shaping layer to provide improved performance. In other aspects, the intake-layer width can be up to a maximum of about 95% of the total, lateral width of the shaping layer 36. The intake-layer width can alternatively be up to about 85% of the total, lateral width of the shaping layer, and can optionally be up to about 75% of the total, lateral width of the shaping layer to provide improved effectiveness.

If the length, width and/or area of the intake layer 32 is too large, the material of the intake layer can be less efficiently used, and the cost of the article can become excessive. The article may also have excessive bulk at its end regions, and the bulk may cause discomfort to the wearer. If the length, width and/or area of the intake layer 32 is too small, liquid may prematurely leak from the pad, and the wearer can feel insecure regarding leakage protection. The wearer may also become less certain about "correctly" placing the article in the undergarment.

The intake layer can be substantially centered (in its machine-direction and cross-direction) with respect to the shaping layer. Optionally, the intake layer may be skewed or offset in one direction (e.g. along the machine-direction), depending on where liquid is expected to first enter the absorbent article.

Figure 5:
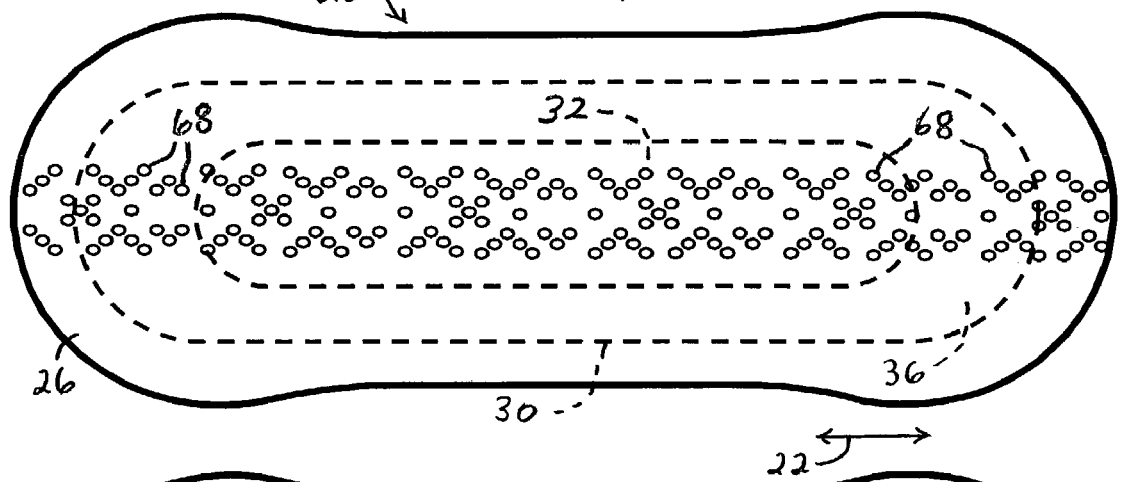
FIG. 5 shows a representative, top view of a bodyside of an absorbent article having a selected pattern of apertures formed into the bodyside surface of the article.
Figure 5A:
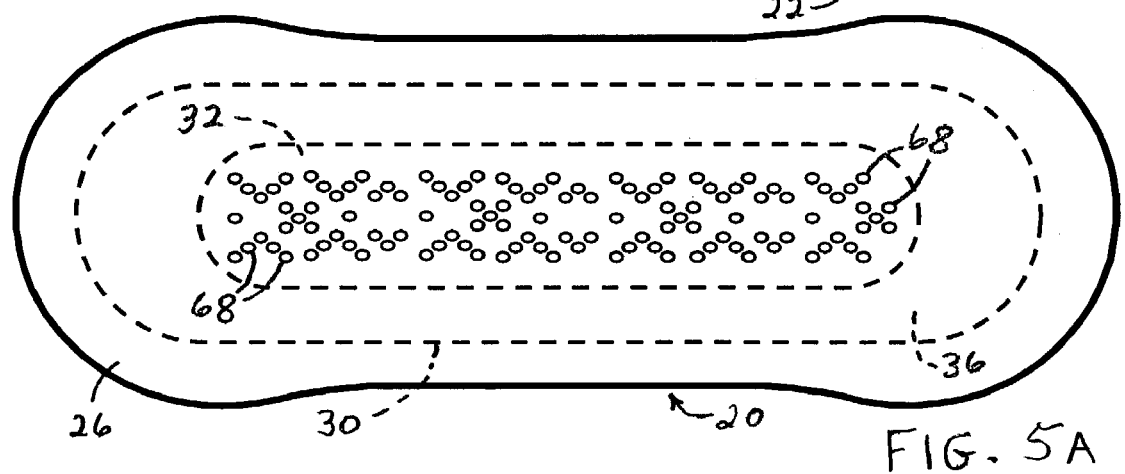
FIG. 5A shows a representative, top view of a bodyside of an absorbent article having another distribution of apertures formed into the bodyside surface of the article.
Figure 5B:
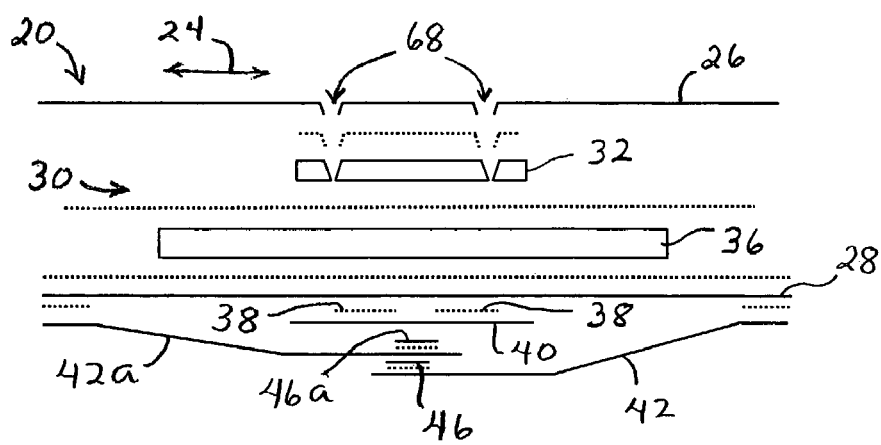
FIG. 5B shows a schematic, expanded view of a representative, transverse cross-section of the absorbent article illustrated in FIG. 5.

The top intake layer 32 may have any operative shape and/or design. For example, the intake layer may include a single piece of material, or multiple pieces of material, such as multiple strips of material. In addition, the intake layer 32 may include holes or apertures 68 (e.g. FIGS. 5 through 5B) to better provide desired liquid-intake properties. The apertures may extend partially or completely through the z-directional thickness of the intake layer 32, as desired.

The shaping layer 36 can provide the functions of liquid storage and retention, liquid distribution, liquid spreading and shape maintenance. The shaping layer may include natural fibers, synthetic fibers, superabsorbent materials, a woven fabric; a nonwoven fabric; a wet-laid fibrous web; a substantially unbonded airlaid fibrous web; an operatively bonded, stabilized-airlaid fibrous web; or the like, as well as combinations thereof. Additionally, the shaping layer may include one or more components that can modify the menses or intermenstrual liquid.

In a particular arrangement, the shaping layer can be a thermally-bonded, stabilized airlaid fibrous web available from Concert Fabrication (Concert code 225.1021), a business having offices located in Gatineaux, Quebec, Canada (e.g. Concert code 225.1021). The shaping layer 36 may optionally be provided by a similar, stabilized airlaid fibrous web available from Buckeye Technologies, Inc., a business having offices located in Memphis, Tenn., U.S.A.

The shaping layer can have a higher basis weight, as compared to the intake layer 32, but may optionally have a similar or equal basis weight. In another feature, the density of the retention/shaping layer 36 can be greater than that of the intake layer 32, and may include a density gradient through the material of the intake layer (e.g. with higher densities positioned relatively closer to the bottom, garment-side of the article). The equal or greater basis weight and higher density of the shaping layer 36 can result in a relatively stiffer material in the bottom retention/shaping layer 36, as compared to the top intake layer 32. The configuration of the shaping layer 36 can better promote liquid transfer to the baffle-side of the article, away from the wearer's skin, and can decrease the likelihood of liquid rewet or flowback to the wearer's skin. Additionally, the shaping layer configuration can reduce the amounts of saturation capacity and retention capacity that are needed to provide a consumer-preferred product.

In a particular aspect, the basis weight of the shaping layer 36 can be at least a minimum of about 100 g/m². The shaping layer basis weight can alternatively be at least about 130 g/m², and can optionally be at least about 165 g/m² to provide improved performance. In other aspects, the basis weight of the shaping layer can be up to a maximum of about 400 g/m², or more. The shaping layer basis weight can alternatively be up to about 350 g/m², and can optionally be up to about 325 g/m² to provide improved effectiveness. In a desired configuration, the shaping layer basis weight can be about 225 g/m².

If the basis weight of the shaping layer 36 is outside the desired values, various disadvantages may occur. For example, an overly high basis weight of the shaping layer can provide a product that is excessively bulky and uncomfortable to the wearer during use. Additionally, the product cost may become too high. An overly low basis weight of the shaping layer can excessively increase the incidence of bunching, twisting and roping of the absorbent pad structure. As a result, the article can excessively leak and reduce consumer confidence in the product performance. Additionally, the liquid transfer from the intake layer to the shaping layer can be excessively decreased, and the absorbent capacity of the shaping layer can become too low. As a result, the article can exhibit excessive leakage and excessive wetness against the wearer's skin.

In a further aspect, the density of the shaping layer 36 can be at least a minimum of about 0.06 g/cm³. The shaping layer density can alternatively be at least about 0.07 g/cm³, and can optionally be at least about 0.08 g/cm³ to provide improved performance. In other aspects, the density of the shaping layer can be up to a maximum of about 0.3 g/cm³, or more. The shaping layer density can alternatively be up to about 0.2 g/cm³, and can optionally be up to about 0.16 g/cm³ to provide improved effectiveness. In a desired arrangement, the density of the shaping layer 36 can be about 0.12 g/cm³.

If the density of the shaping layer 36 is outside the desired values, various disadvantages may occur. For example, an overly high density of the shaping layer can provide an excessively stiff article which is uncomfortable during use. Additionally, depending the basis weight and thickness of the shaping layer, the absorbent structure can exhibit excessive bunching, twisting and roping, and can cause discomfort and poor fit. An overly high density can excessively reduce the permeability and absorbent capacity of the shaping layer. As a result, the liquid transfer can be poor, and the article can prematurely leak. In a stabilized airlaid web that contains superabsorbent material, an overly high density can excessively restrict the ability of the superabsorbent material to swell and absorb liquid. This can decrease the saturation capacity and retention capacity of the web, and can lead to premature leakage. Additionally, during production of the high density web, the high compression employed to densify the web can damage the superabsorbent material and degrade its performance. This again can allow premature leakage and excessive wetness against the wearer's skin. An overly low density in the shaping layer can provide a product that is too thick, ill fitting, and uncomfortable. Also, the permeability of the shaping layer can become too high, and the shaping layer may be unable to adequately desorb the intake layer. As a result, there can be excessive rewet and flowback of liquid to the wearer's skin.

In another aspect, the shaping layer 36 can include a distinctive total absorbent saturation capacity. The total absorbent saturation capacity of the shaping layer can be at least a minimum of about 5 grams of menses simulant A (5 g). The shaping layer saturation capacity can alternatively be at least about 20 g, and can optionally be at least about 30 g to provide improved performance. In other aspects, the saturation capacity of the shaping layer can be up to a maximum of about 100 grams of menses simulant A (100 g), or more. The shaping layer saturation capacity can alternatively be up to about 75 g, and can optionally be up to about 70 g to provide improved effectiveness. In a desired configuration, the shaping layer saturation capacity can be about 45 g.

In still another aspect, the shaping layer 36 can Include a distinctive total absorbent retention capacity. The total absorbent retention capacity of the shaping layer 36 can be at least a minimum of about 5 grams of menses simulant A (5 g). The shaping layer retention capacity can alternatively be at least about 6 g, and can optionally be at least about 8 g to provide improved performance. In other aspects, the total absorbent retention capacity of the shaping layer can be up to a maximum of about 30 g, or more. The shaping layer retention capacity can alternatively be up to about 25 g, and can optionally be up to about 17 g to provide improved effectiveness. In a desired configuration, the shaping layer retention capacity can be about 12 g.

In still a further aspect, the shaping layer 36 can include a distinctive, specific absorbent saturation capacity. The specific absorbent saturation capacity of the shaping layer can be at least a minimum of about 1 gram of menses simulant A per gram of shaping layer material (1 g/g). The shaping layer specific saturation capacity can alternatively be at least about 5 g/g, and can optionally be at least about 10 g/g to provide improved performance. In other aspects, the specific saturation capacity of the shaping layer can be up to a maximum of about 30 grams of menses simulant A per gram of shaping layer material (30 g/g), or more. The shaping layer specific saturation capacity can alternatively be up to about 25 g/g, and can optionally be up to about 20 g/g to provide improved effectiveness. In a desired configuration, the shaping layer specific saturation capacity can be about 15 g/g. Additionally, the shaping layer can include superabsorbent material to help provide the desired, specific saturation capacity.

An additional aspect of the shaping layer 36 can include a distinctive, specific absorbent retention capacity. The specific absorbent retention capacity of the shaping layer can be at least a minimum of about 1 gram of menses simulant A per gram of shaping layer material (1 g/g). The shaping layer specific retention capacity can alternatively be at least about 1.5 g/g, and can optionally be at least about 2 g/g to provide improved performance. In other aspects, the specific absorbent retention capacity of the shaping layer can be up to a maximum of about 10 g/g, or more. The shaping layer specific retention capacity can alternatively be up to about 8 g/g, and can optionally be up to about 7 g/g to provide improved effectiveness. In a desired arrangement, the shaping layer specific retention capacity can be about 4 g/g. Additionally, the shaping layer can include superabsorbent material to help provide the desired, specific retention capacity.

A further feature can include a shaping layer 36 wherein the shaping layer materials (e.g. fibers) are configured to provide a shaping layer that is more "hydrophilich" than the intake layer 32. Additionally, the shaping layer can have a distinctive shaping-layer area. In particular aspects, the shaping-layer area can be at least a minimum of about 100 cm², and can be not more than a maximum of about 150 cm². In another feature, the area can be distinctively larger than the area of the intake layer 32. In a particular aspect, the shaping-layer area can be at least a minimum of about 1.33 times the intake-layer area (1.33×). The shaping-layer area can alternatively be at least about 1.5 times the intake-layer area, and can optionally be at least about 1.67 times the intake-layer area to provide improved performance. In other aspects, the shaping-layer area can be up to a maximum of about 5 times the intake-layer area, or more. The shaping-layer area can alternatively be up to about 4 times the intake-layer area, and can optionally be up to about 3.33 times the intake-layer area to provide improved effectiveness. In a desired arrangement the shaping-layer area can be about 2.4 times the intake-layer area.

In another feature, the shaping layer 36 can include a distinctive stiffness value. In particular aspects, the stiffness of the shaping layer can be at least a minimum of about 7.5 grams and can be not more than a maximum of about 8.5 grams, as determined by the cantilever bending test previously described in the present disclosure. Additionally, the shaping layer 36 can provide an improved resilience to the article 20. In a particular feature, the cross-directional width of the absorbent body 30 after ordinary use by the wearer can be at least a minimum of about 90% of the original width of the absorbent body.

The bottom baffle-side shaping layer 36 which can further provide an improved retention layer, the size of which can be configured to allow for the greatest fluid capacity potential (i.e., largest area for liquid retention). The properties required for the liquid retention in this bottom layer are synergistic with properties needed to help maintain the shape of the pad.

The shaping layer 36 can be designed with a greater density and higher basis weight to provide improved liquid distribution and retention. These properties can also lead to a greater stiffness than the top layer, and can allow the bottom layer to better maintain the shape of the absorbent pad structure during wear.

The addition of a binder fiber or other binder material in the bottom retention/shaping layer 36 can help maintain the integrity and shape of the shaping layer and article during ordinary wear. In a desired feature, the bottom retention/shaping layer 36 can have a good x-y direction resiliency for better shape-maintenance, versus having z-direction resiliency for intake. The retention/shaping layer may also include a super absorbent material to provide greater absorbent capacity, and to provide a better ability to 'lock in' and hold the absorbed liquid. The retention/shaping layer may include any operative shape and/or design. In particular, the shape and design of the shaping layer 36 can be configured to allow the product to better fit the user's body and/or undergarment.

The present design results in a bottom retention/shaping layer 36 that provides product shaping properties, whereas the top intake layer does not need to have product shaping properties. For example, it requires a greater force to compress the bottom retention/shaping layer in the cross direction versus the top intake layer.

In a desired configuration, the material of the shaping layer 36 can have a distinctive peak load to compress value, and the peak load to compress value of the shaping layer 36 can be relatively greater than that of the intake layer 32. In a particular aspect, the material of the shaping layer 36 can have a peak load to compress value which is within the range of about 700-1500 grams. In comparison, the peak load to compress value of the intake layer material can be within the range of about 200-300 grams.

The "peak load to compress" value is the amount of force needed to compress a test sample to 50% of its original thickness dimension. The peak load to compress value can be determined by employing the following method. A 2 inch by 12 inch (5.1 cm×30.5 cm) piece of sample material is cut with its longer dimension aligned with the longitudinal direction of the product or raw material web. The weight of the sample is determined. The thickness of the material is determined under a 0.2 psi (1.38 KPa) load. The material is formed into a cylinder having a height of 2 inches (5.1 cm), and with the two ends having 0-0.125 inch (0-3.18 mm) overlap, the material is stapled together with three staples. One staple is near the middle of the width of the sample, the other two nearer each edge of the width of the material. The longest dimension of the staple is in the circumference of the formed cylinder to minimize the effect of the staples on the testing.

An INSTRON tester or similar instrument is configured with a bottom platform, a platen larger than the circumference of the sample to be tested and parallel to the bottom platform, attached to a compression load cell placed in the inverted position. The specimen is placed on the platform, under the platen. The platen is brought into contact with the specimen and compresses the sample at a rate of 25 mm/min. The maximum force obtained in compressing the sample to 50% of its width (1 inch) (2.54 cm) is recorded.

If the material buckles, it is typical for the maximum force to be reached before the sample is compressed to 50%. In a product where the length of the absorbent is less than 12 inches (30.5 cm), the Edgewise Compression value of the material can be determined in the following manner. A detailed discussion of the edge-wise compression strength has been given in *The Handbook Of Physical And Mechanical Testing Of Paper And Paperboard*, Richard E. Mark editor, Dekker 1983, (Vol. 1). Based on theoretical models governing buckling stresses, in the Edge-wise Compression configuration described, the buckling stress is proportional to $E*t^2/(H^2)$ with the proportionality constant being a function of $H^2/(R*t)$ where E is the Elastic modulus, H is the height of the cylinder, R is the radius of the cylinder, and t is the thickness of the material. Expressing the stress in terms of force, it can be shown that the parameter that needs to be maintained constant is $H^2/R$. Therefore, for a sample that is smaller than 12 inches (30.5 cm), the largest possible circle should be constructed and its height (width of the sample being cut out) adjusted such that $H^2/R$ equals 2.1 inches (5.3 cm).

As stated earlier, an important property of the top intake layer is to pull liquid into the pad and down to the bottom retention, shaping layer. Saturation capacity, retention capacity, liquid allocation and liquid distribution data show that the top intake layer material can hold at least a minimum of about 10% of the total amount of liquid absorbed by the intake layer and shaping layer. The percentage held by the intake layer can alternatively be at least about 12%, and can optionally be at least about 15% to provide improved performance. In other aspects, the percentage held by the intake layer can be up to a maximum of about 40%, or more. The percentage held by the intake layer can alternatively be up to about 37%, and can optionally be up to about 35% to provide improved effectiveness. In a desired arrangement, the percentage held by the intake layer can be about 20%

In a further aspect, the shaping layer material can hold at least a minimum of about 60% of the total amount of liquid absorbed by the intake layer and shaping layer. The percentage held by the shaping layer can alternatively be at least about 62%, and can optionally be at least about 65% to provide improved performance. In other aspects, the percentage held by the shaping layer can be up to a maximum of about 90%, or more. The percentage held by the shaping layer can alternatively be up to about 87%, and can optionally be up to about 85% to provide improved effectiveness. In a desired arrangement, the percentage held by the shaping layer can be about 80%

The specific saturation capacity and the specific retention capacity can be determined by soaking a 1 inch by 1 inch (2.54 cm×2.54 cm) sample of absorbent material in an amount of simulant A that is sufficient to fully saturate the sample (e.g. 30 mL) for 30 minutes. The wet absorbent is then placed between a layer of through-air-bonded-carded web material and a layer of blotter paper, and a pressure of 0.05 psi (0.345 KPa) is applied for 1 minute to remove any pools of liquid. The saturated sample is then weighed. The weight of liquid held in the sample divided by the dry weight of the sample is the specific saturation capacity of the sample.

After the saturated sampled is weighed, the absorbent sample is placed in a centrifuge and spun at 300 G for 3 minutes. The spun sample is then weighed. The weight of the liquid remaining in the spun sample divided by the dry weight of the sample is the specific retention capacity of the sample. Accordingly:
  a. Saturation Capacity=(Wet Wt. Before Centrifuge—Dry Wt.)/(Dry Wt.)
  b. Retention Capacity=(Wet Wt. After Centrifuge—Dry Wt.)/(Dry Wt.)

The total absorbent saturation capacity of an overall layer or other component can be determined by multiplying its specific saturation capacity times the total weight of such component. Similarly, total absorbent retention capacity of an overall layer or other component can be determined by multiplying its specific retention capacity times the total weight of such component.

A suitable through-air-bonded-carded web material has a 2.5 osy (84.8 g/m$^2$) basis weight, a 0.024 g/cm3 density, and is composed of 60 wt % of 6 denier, KoSa type 295 polyester fiber; and 40 wt % of 3 denier, Chisso ESC-HR6 bicomponent fiber. The polyester fiber is available from KoSa, a business having offices located in Charlotte, N.C., U.S.A., and the bicomponent fiber is available from Chisso Corporation, a business having offices located in Osaka, Japan. A suitable blotter paper is 100-lb VERIGOOD white blotter paper available from Fort James Corporation, a business having offices located in Menasha, Wis., U.S.A. (e.g. product item number 411-01012). Substantially equivalent materials may optionally be employed.

The Fluid Allocation and Distribution values can be obtained by providing a "system" sample composed of, from top to bottom, a cover layer, an intake layer, a shaping layer and a film baffle. The sample size is 4 inches by 5 inches (10.2 cm×12.7 cm) for all layers. A pressure of 0.25 psi (1.72 KPa) is applied to the sample and a continuous flow of menses simulant B is directed into the sample a flow rate of 2.5 mL per hour to provide a total menses simulant volume of 60 mL, resulting in a total flow time of 2.4 hours The amount of simulant B held in the various layers can then be measured. Menses simulant B is swine blood diluted to a hematocrit level of 30% by volume, with sheared, thick egg white added to mimic the mucin component of menses. This simulant is available from Cocalico Biologicals, Inc., a business having offices located in Reamstown, Pa., U.S.A.; and is also described in U.S. Pat. No. 5,883,231 entitled MENSES SIMULANT by A. Achter et al. granted Mar. 16, 1999, the entire disclosure of which is incorporated herein in a manner that is consistent herewith.

The amount of superabsorbent material in the shaping layer 36 can be up to about 75 wt %, as determined with respect to the total weight of material in the shaping layer 36. In particular aspects, the amount of superabsorbent material can be within the range of about 5-35 wt %, and can alternatively be within the range of about 8-20 wt % to provide improved performance. In desired configurations, the amount of superabsorbent can be about 15 wt %.

If the amount of superabsorbent is outside the desired values, various disadvantages may arise. For example, the fit and comfort of the article can be adversely affected. An overly large amount of superabsorbent can cause gel-containment difficulties and cause excessive gel on the wearer's skin. Additionally, the transfer of liquid to the shaping layer may be inhibited or the product may have inadequate saturation and retention capacity, causing leakage and excessive wetness against the wearer's skin. The manufacturing costs can also become excessive.

In a desired feature, the top (bodyside) intake layer 32 of the present invention can be smaller in size than the bottom retention/shaping layer 36. Accordingly, the bottom retention/shaping layer 36 should be larger than the top intake layer, and can substantially define the overall size of the absorbent body 30.

A further feature of the article 20 can include a configuration which provides a density gradient between the constituent strata or layers of the absorbent body 30, and the shaping layer 36 and the intake layer 32 can have a distinctive density ratio. In a particular aspect, the density ratio of the shaping layer density to the intake layer density can be at least a minimum of about 0.03. The density ratio can alternatively be at least about 0.2, and can optionally be at least about 0.3 to provide improved performance. In other aspects, the density ratio of the shaping layer density to the intake layer density can be up to a maximum of about 1. The density ratio can alternatively be up to about 0.9, and can optionally be up to about 0.8 to provide improved effectiveness.

If the density ratio is outside the desired values, the absorbent structure can exhibit poor transfer of liquid from the intake layer to the shaping layer. As a result, there can be a poor partitioning of liquid in the absorbent structure with an excessive amount of liquid held in the intake layer. This can allow premature leakage and allow increased wetness against the wearer's skin.

A further feature of the article can include a configuration which provides a basis weight gradient between the layers of the absorbent body, and the intake layer and the shaping layer can provide a distinctive basis weight ratio.

In a particular aspect, the basis weight ratio of the intake layer to the shaping layer can be at least a minimum of about 0.08. The basis weight ratio can alternatively be at least about 0.3, and can optionally be at least about 0.43 to provide improved performance. In other aspects, the basis weight ratio of the intake layer to the shaping layer can be up to a maximum of about 1. The basis weight ratio can alternatively be up to about 0.95, and can optionally be up to about 0.89 to provide improved effectiveness. In a desired arrangement, the ratio can be about 0.8.

If the basis weight ratio is outside the desired values, the absorbent structure can exhibit a poor transfer of liquid from the intake layer to the shaping layer. This can cause a poor liquid partitioning of the liquid, with an excessive amount held in the intake layer. As a result, the article may have premature leakage and increased wetness against the skin.

In a further aspect, the absorbent structure can provide a distinctive ratio of the total absorbent saturation capacity of the intake layer to the total absorbent saturation capacity of the shaping layer. The component, total-saturation capacity ratio can be at least a minimum of about 0.01. The total-saturation capacity ratio can alternatively be at least about 0.1, and can optionally be at least about 0.16 to provide improved performance. In other aspects, the component, total-saturation capacity ratio can be up to a maximum of about 1. The total-saturation capacity ratio can alternatively be up to about 0.85, and can optionally be up to about 0.75 to provide improved effectiveness. In a desired configuration, the total-saturation capacity ratio can be about 0.3.

In another feature the absorbent structure can provide a distinctive ratio of the total absorbent retention capacity of the intake layer to the total absorbent retention capacity of the shaping layer. The component, total-retention capacity ratio can be at least a minimum of about 0.01. The total-retention capacity ratio can alternatively be at least about 0.05, and can optionally be at least about 0.09 to provide improved performance. In other aspects, the component, total-retention capacity ratio can be up to a maximum of about 0.76. The total-retention capacity ratio can alternatively be up to about 0.6, and can optionally be up to about 0.47 to provide improved effectiveness. In a desired configuration, the total-saturation capacity ratio can be about 0.2.

If the capacity ratios are outside the desired values, the absorbent structure can exhibit a poor transfer of liquids from the intake layer to the shaping layer. This can cause a poor partitioning of liquid, with an excessive amount of liquid remaining in the intake layer. As a result, the article may have excessive leakage and may allow excessive wetness against the skin.

A further aspect of the invention can include an intake layer 32 which has a distinctive aperturing or co-aperturing pattern (e.g. Snowflake pattern). Apertures or co-apertures can generally increase the rate at which bodily liquids can move through the thickness of the material or materials and may also provide a visual cue to consumers of improved leakage performance. Aperturing involves creating openings in a material, while co-aperturing can create openings in two or more materials. Aperturing and co-aperturing may create openings partially through the material or materials, or may create openings completely through the material or materials. A particular configuration can, for example, include a co-aperturing of the cover and the intake layer. Alternate arrangements can include a co-aperturing of the intake layer and the shaping layer, a co-aperturing of the cover and the shaping layer, or a co-aperturing of the cover, the intake layer and the shaping layer. The intake layer may alternatively have another operative aperturing pattern in which the aperture or co-aperture density (concentration) provides a percent open area which is not more than about 15%. In particular aspects, the percent open area can be less than a maximum of about 5%, and can alternatively be less than about 2% to provide improved effectiveness. In a desired arrangement, the percent open area can be less than about 2.6%.

An excessively high concentration of apertures or co-apertures in the material of the relatively low density intake layer can adversely affect the function of that material. Too high a concentration of apertures or co-apertures in a low density intake layer can increases the time required to take liquid into the layer, which could, in turn, can result in early leakage and pooling of liquid on the surface of the article giving a larger stain size and increased wetness against the skin during use. Additionally, having an excessively large number of apertures in the low density intake layer 32 can result in a higher rewetting of liquid from other components of the article, such as the reservoir/shaping layer of the article, and can result in an excessively wet and uncomfortable bodyside surface of the article.

The distinctive aperturing or co-aperturing design for the relatively low basis weight material in the intake layer 32 can result in reduced intake times. The resultant intake layer material can have less disruption of the density and saturation capacity of the material, and can provide reduced stain size, reduced stain propagation during use, and reduced rewet. The aperturing or co-aperturing pattern can facilitate liquid flow into and through the low density absorbent materials of the intake layer while maintaining a desired visual cue provided by the apertures and/or co-apertures. In addition, the relatively fewer holes of the aperturing or co-aperturing pattern employed in the present invention can allow the use of higher web tensions during manufacturing operations, and can help to improve the formation and definition of desired embossing patterns on the article.

The aperture density (concentration) is the aperture area per unit area of intake layer:

$$(\text{area/aperture}) \cdot (\text{number of apertures}) \div (\text{total area of the intake layer}).$$

Figure 4:
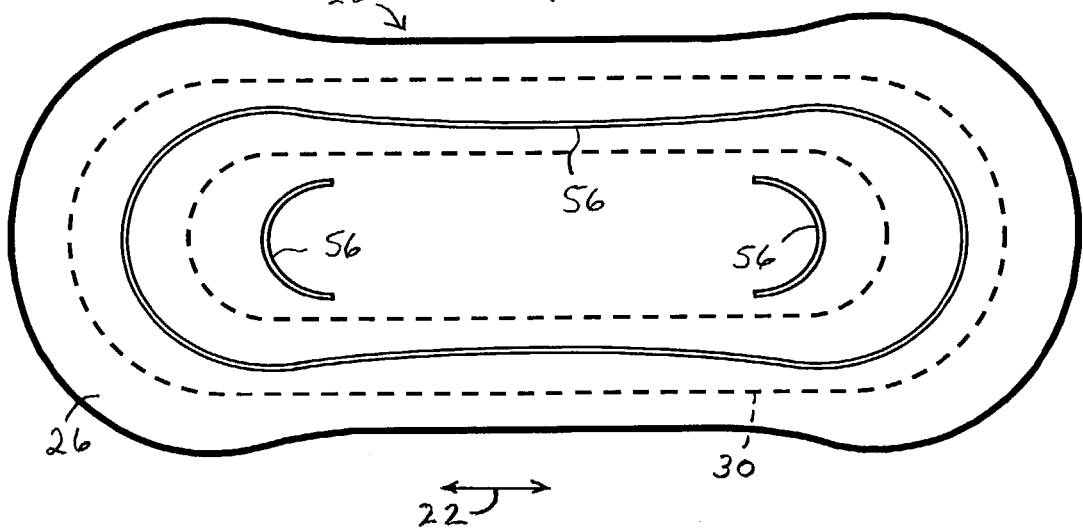
FIG. 4 shows a representative, top view of a bodyside of an absorbent article having a selected pattern of embossments formed into the article.
Figure 4A:
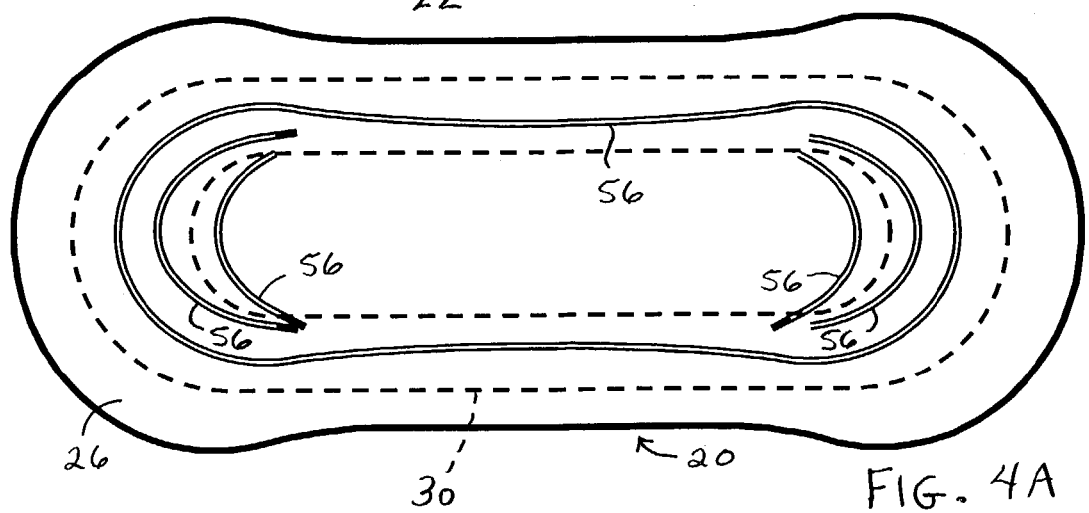
FIG. 4A shows a representative, top view of a bodyside of an absorbent article having another distribution of embossments formed into the article.
Figure 4B:
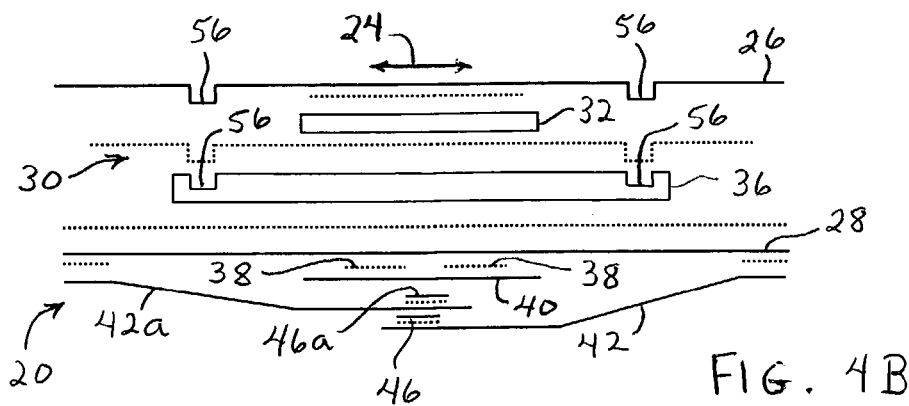
FIG. 4B shows an expanded, schematic view of a representative, transverse cross-section of the absorbent article illustrated in FIG. 4.

In optional arrangements, the article 20 may include additional components or component layers, as desired. For example, a transfer layer may be positioned between the intake layer 32 and the shaping layer 36. In another feature, the article may include any desired pattern of embossments 56 (e.g. FIGS. 4 through 4B) formed into at least the bodyside surface of the article. The embossing can deform the bodyside of the cover and can deform selected portions of the absorbent body 30 to provide operative channel regions that can help block, direct or otherwise control a desired movement of liquids along the bodyside surface of the article. The embossing can also provide an aesthetic benefit to the consumer, and a visual cue regarding fit and leakage protection. In particular arrangements, the embossments can be positioned generally adjacent the perimeter edges of the absorbent body 30. In other aspects, the embossments can be configured to provide a regular or irregular pattern having one or more channels which are distributed in a symmetrical or asymmetrical array, as desired.

The article 20 can include a system of side-panel or wing portions 42 which can be integrally connected to appointed sections of the side regions 60 along the intermediate portion of the article. For example, the side-panels or wings can be separately provided members that are subsequently attached or otherwise operatively joined to the intermediate portion of the article 20 (e.g. FIGS. 1 through 1C).

Figure 2:
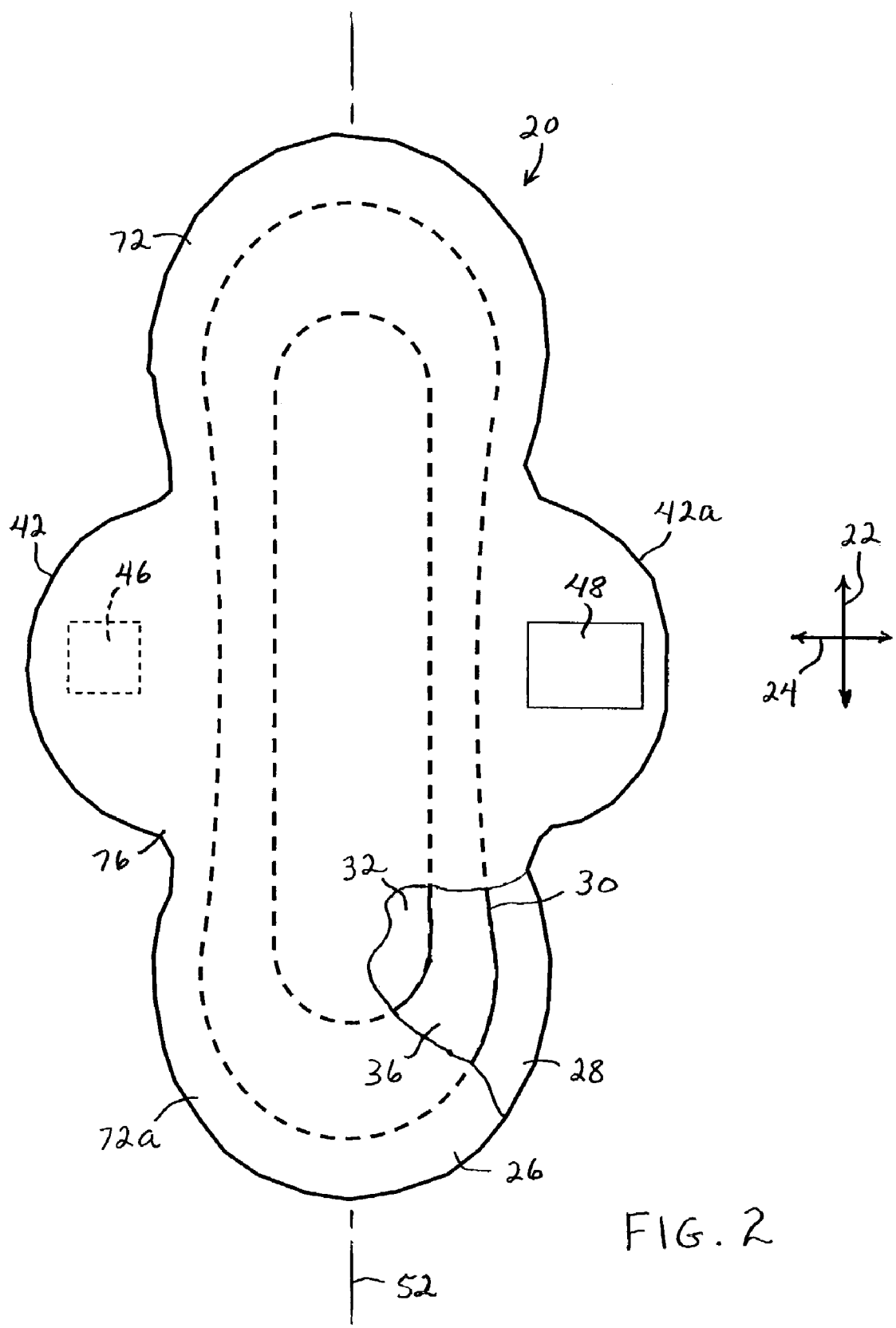
FIG. 2 shows a representative, partially cut-away, top, plan view of a bodyside of an absorbent article having side-panels or wings that have been unitarily formed with one or more components of the article, where the wings include a system of interengaging mechanical fasteners.

In other configurations, the wings or side-panels 42 can be unitarily formed with one or more components of the article. As representatively shown in FIGS. 2 through 3C, for example, either or both wing portions may be formed from a corresponding, operative extension of the material employed to form the cover 26. Alternatively, either or both wing portions may be formed from a corresponding, operative extension of the material employed to form the baffle 28, or formed from a corresponding, operative combination of the cover and baffle materials.

Figure 2A:
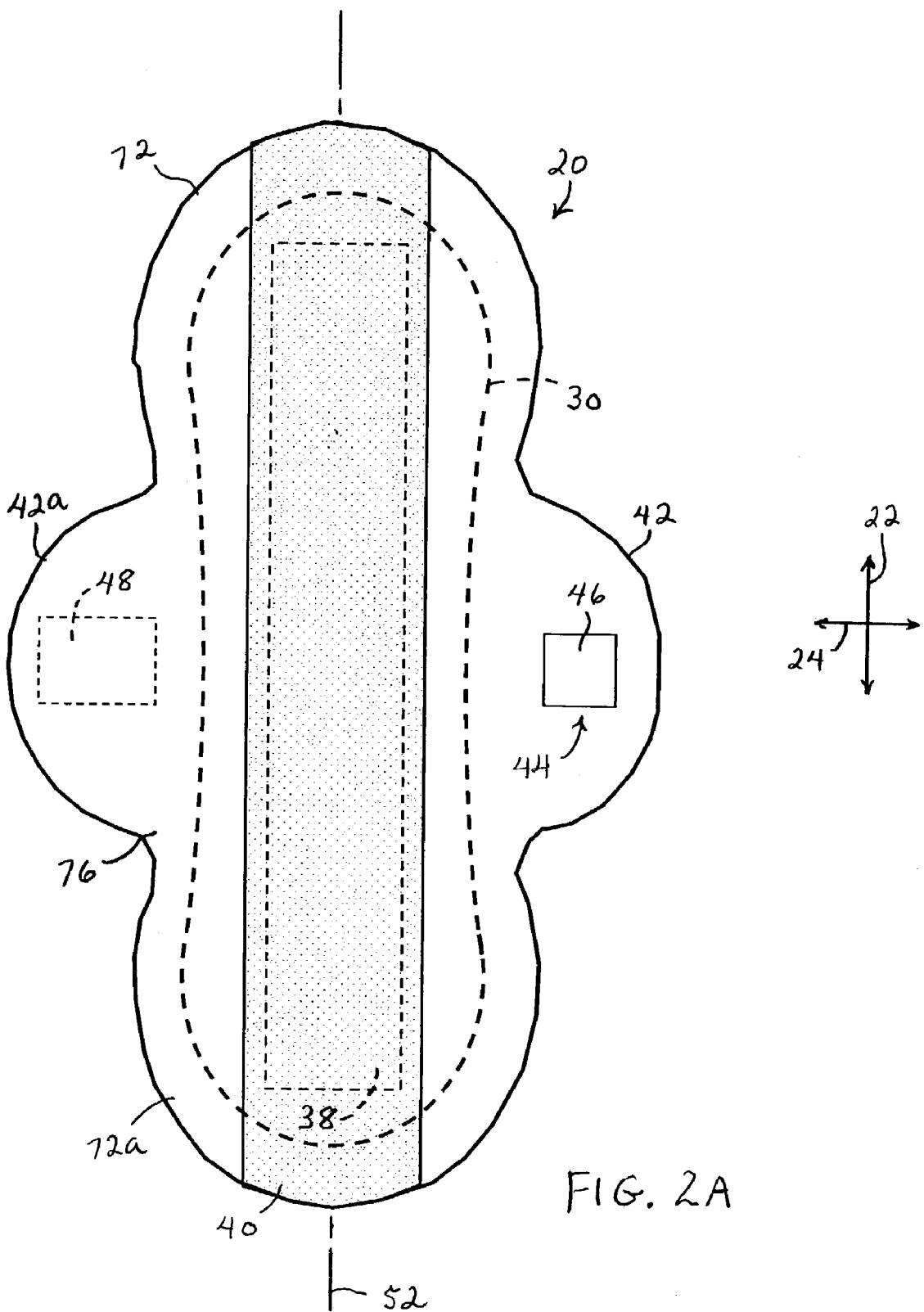
FIG. 2A shows a representative, bottom, plan view of a garment-side of the absorbent article illustrated in FIG. 2.
Figure 2B:
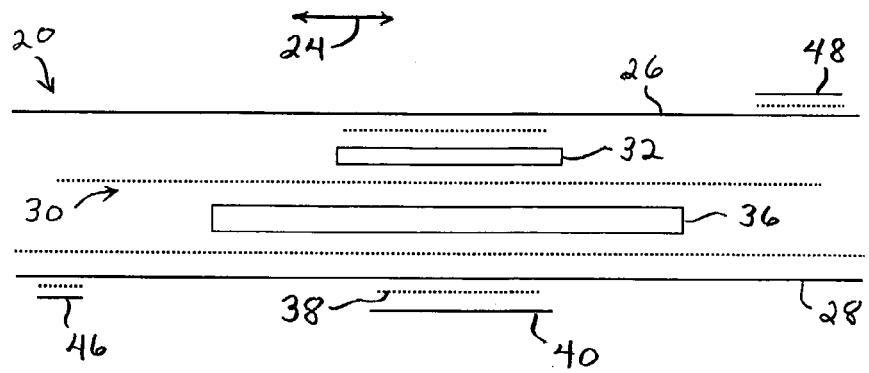
FIG. 2B shows an expanded, schematic view of a representative, transverse cross-section of the absorbent article illustrated in FIG. 2.
Figure 2C:
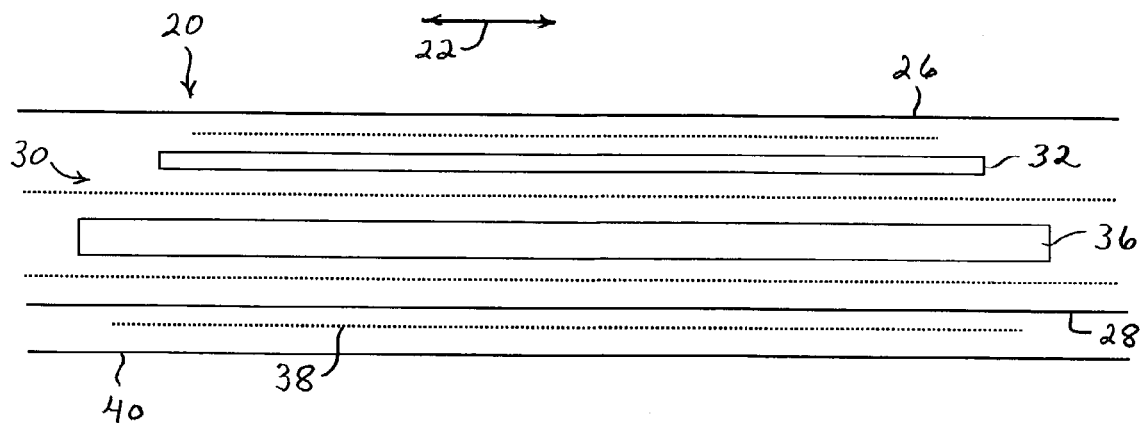
FIG. 2C shows an expanded, schematic view of a representative, longitudinal cross-section of the absorbent article illustrated in FIG. 2.

The side-panels can have an appointed storage position (e.g. FIGS. 1A through 1C) in which the side-panels 42 are directed generally inwardly toward the longitudinally-extending centerline 52. As illustrated, the side-panel that is connected to one side margin may have sufficient cross-directional length to extend and continue past the centerline 52 to approach the laterally opposite side margin of the article. The storage position of the side-panels can ordinarily represent an arrangement observed when article is first removed from its wrapper or other packaging. Prior to placing the article into a bodyside of an undergarment prior to use, the side-panels 42 can be selectively arranged to extend laterally from the side regions 60 of the article intermediate portion (e.g. FIGS. 2 and 2A). After placing the article in the undergarment, the side-panels 42 can be operatively wrapped and secured around the side edges of the undergarment to help hold the article in place.

Additionally, a selected configuration of garment adhesive 38, such as the illustrated strip regions, may be distributed onto the garment-side of the article to help secure the article to the undergarment. Typically, the garment adhesive can be distributed over the garment-side of the baffle, and one or more layers or sheets of release material 40 can be removably placed over the garment adhesive during storage prior to use.

The side-panel portions 42 can have any operative construction, and can include a layer of any operative material. Additionally, each side-panel can comprise a composite material. For example, the side-panels may include a spunbond fabric material, a bi-component spunbond material, a necked spunbond material, a neck-stretched-bonded-laminate (NBL) material, a meltblown fabric material, a bonded carded web, a thermal bonded carded web, a through-air bonded carded web or the like, as well as combinations thereof.

Each side-panel 42 can be joined to its corresponding side region 60 of the article in any operative manner. For example, the side-panel can be joined to the cover 26, the baffle 28 or another article component, as well as any combination thereof. In the illustrated example, each side-panel 42 is joined to the outward, garment-side surface of the baffle 28, but may optionally be joined to the bodyside surface of the baffle. The side-panel can be attached with hotmelt adhesive, but any other operative adhesive or attachment mechanism may alternatively be employed.

In another feature, each side-panel portion 42, or any desired combination of the employed side-panel portions, can include a panel-fastener component 44 which is operatively joined to an appointed engagement surface of its associated side-panel. The panel-fastener can be configured to operatively attach to the wearer's undergarment and/or to any appointed, landing-zone portion of the article 20. For example, the panel-fastener can include a system of interengaging mechanical fasteners, a system of adhesive fasteners, a system of cohesive fasteners or the like, as well as combinations thereof.

With reference to FIGS. 1A through 2C, for example, either or both side-panels 42 can include a hook or other "male" component 46 of an interengaging mechanical fastener system. Any operative hook component may be employed. For example, a suitable hook component materials can include a J-hook, mushroom-head hook, flat-top nailhead hook, a palm-tree hook, a multiple-J hook or the like, as well as combinations thereof.

Figure 3:
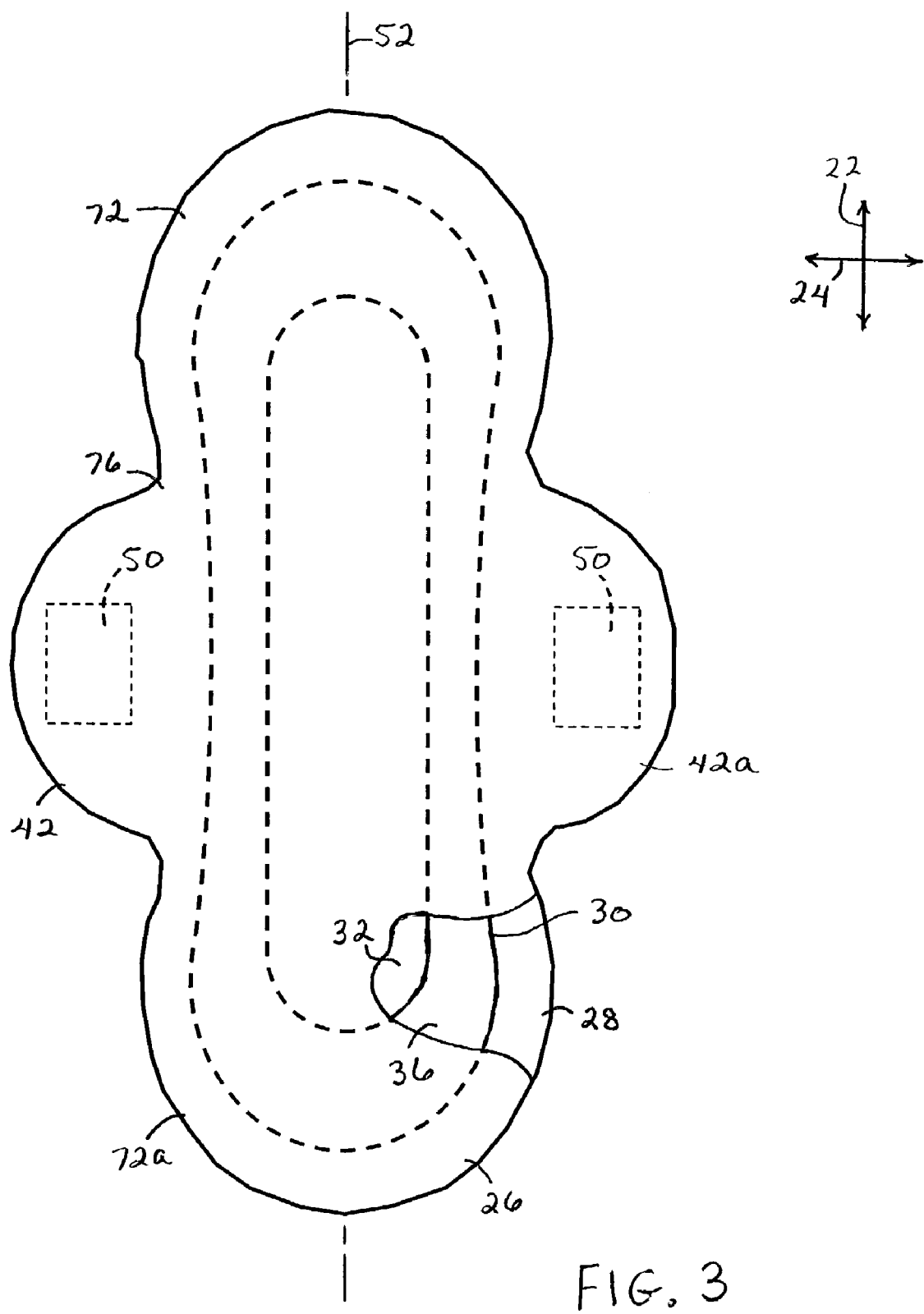
FIG. 3 shows a representative, partially cut-away, top, plan view of a bodyside of an absorbent article having side-panels or wings that have been unitarily formed with one or more components of the article, where the wings include a system of adhesive fasteners.
Figure 3A:
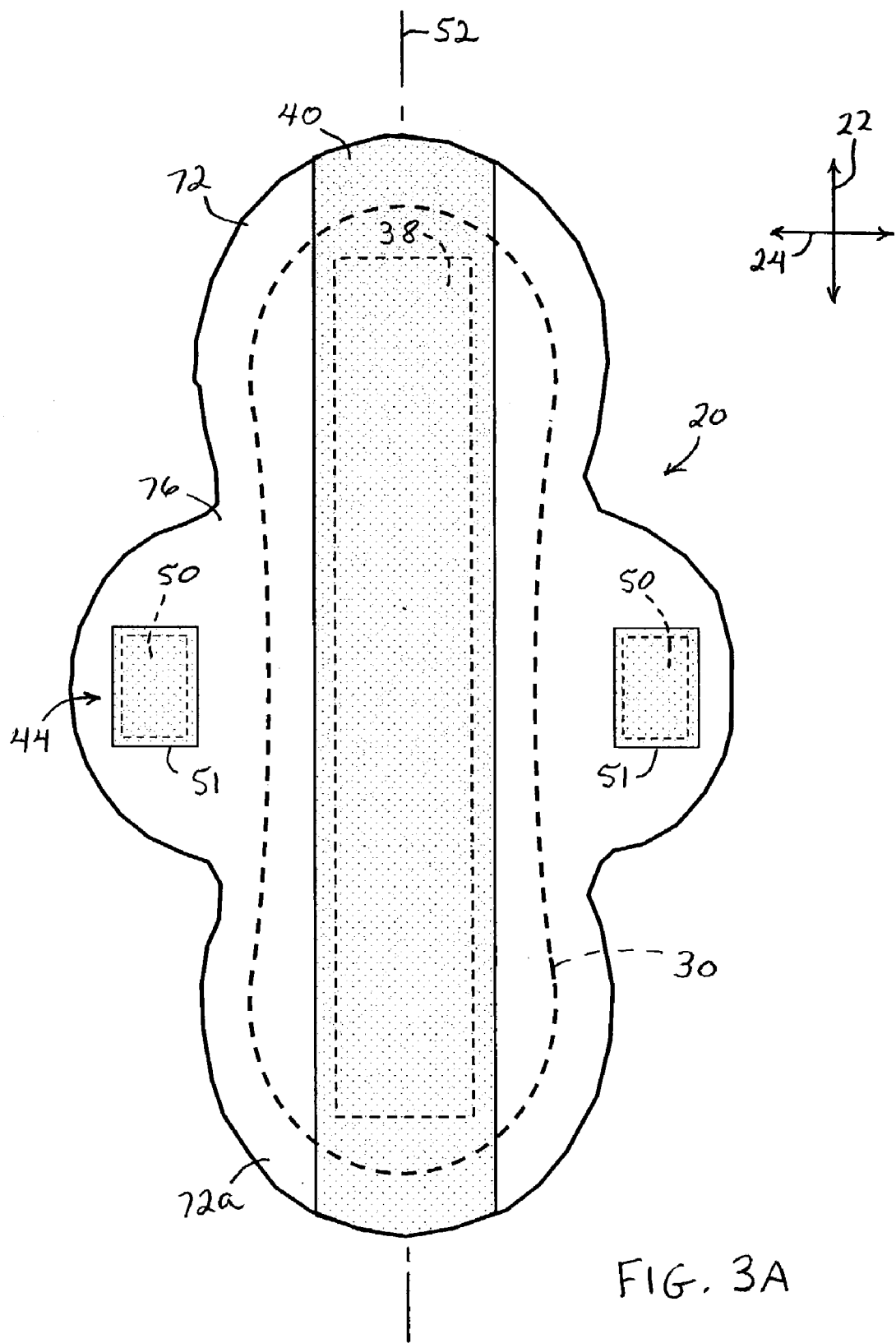
FIG. 3A shows a representative, bottom, plan view of a garment-side of the absorbent article illustrated in FIG. 3.
Figure 3B:
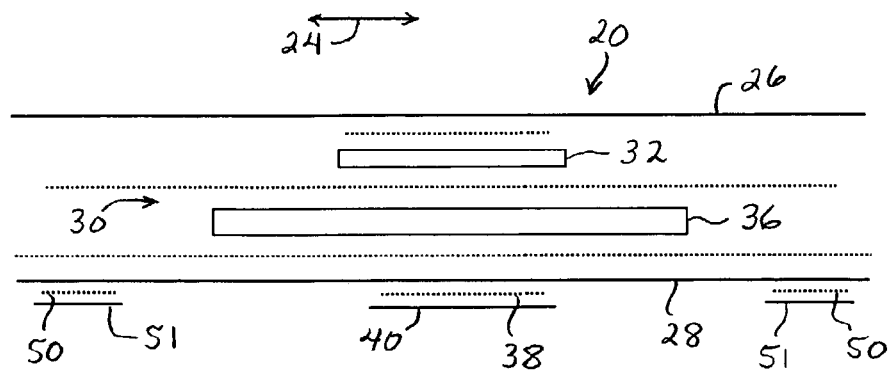
FIG. 3B shows an expanded, schematic view of a representative, transverse cross-section of the absorbent article illustrated in FIG. 3.
Figure 3C:
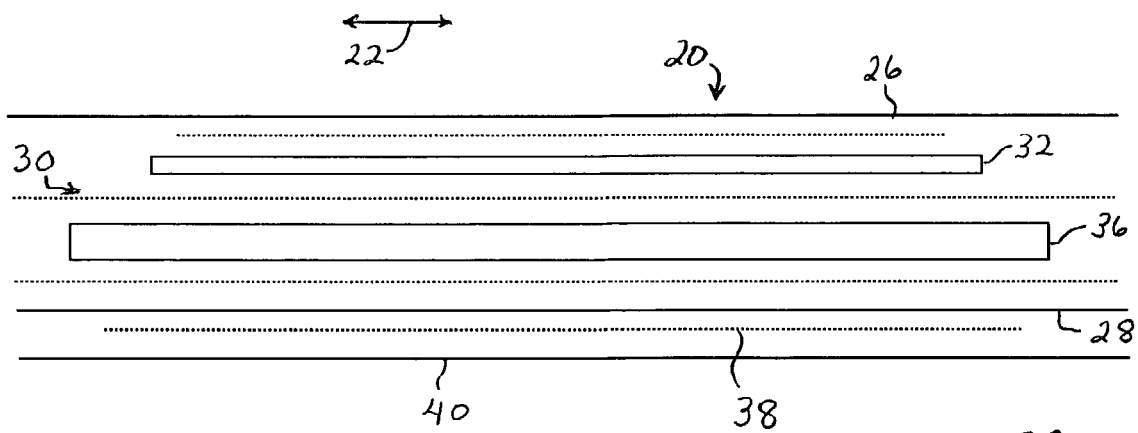
FIG. 3C shows an expanded, schematic view of a representative, longitudinal cross-section of the absorbent article illustrated in FIG. 3.

With reference to FIGS. 3 through 3C, for example, either or both side-panels 42 can include a panel-fastener system 44 which alternatively incorporates an operative adhesive 50. The adhesive may be a solvent-base adhesive, a hotmelt adhesive, a pressure-sensitive adhesive, or the like, as well as combinations thereof. Each section of adhesive 50 may be covered with a removable release sheet 51.

An operative first section of the selected hook component 46 can be joined to a major facing surface of at least a first side-panel portion 42, and can be configured to contact or otherwise engage a cooperating loop material 48 provided on a second side-panel portion 42a during ordinary use, as representatively shown in FIG. 1A and 1B. Additionally, an operative second section of a hook component 46a, composed of the same or different type of hook material, can be joined to a major facing surface of the second side-panel portion 42a, and can be configured to contact or otherwise engage an outward surface of the wearer's undergarment during ordinary use. For example, the hook component can be arranged to operatively engage and removably attach to the outward surface of a crotch region of the undergarment.

Each side-panel portion 42, or any desired combination of the employed side-panel portions, can include a loop or other "female" component 48 of an interengaging mechanical fastener system. Any operative loop component may be employed. For example, a suitable loop component material can include a woven fabric, a knit fabric, a nonwoven fabric, a fabric laminated to a substrate or the like, as well as combinations thereof. The loop material may be integrally formed with or otherwise provided by the material of its corresponding side-panel portion. Optionally, the loop material may be a separately provided component of that is subsequently assembled to its corresponding side-panel portion.

An operative first section of a selected loop component 48 can be joined to a major facing surface of at least the second side-panel portion 42a, and can be configured to contact or otherwise engage the hook component 46 on the first side-panel portion 42 during ordinary use, as representatively shown in FIGS. 1A and 1B. Additionally, an operative second section of a loop component 48a, composed of the same or different type of loop material, can be joined to a major facing surface of the first side-panel portion 42. As a result, the user can have the option of alternatively attaching the second hook component 46a of the second side-panel onto the second loop component 48a of the first side-panel. Accordingly, the first hook component 46 may alternatively be engaged with the outward surface of the wearer's undergarment.

Each or any desired combination of the provided loop components (48, 48a) may be a separately provided member that is subsequently joined and assembled to its corresponding side-panel portion (42a, 42). In a desired feature, each or any desired combination of the provided loop components can be integrally provided by the material employed to construct its corresponding side-panel portion.

In the various arrangements of the present invention, the hook component 46 can be configured to have a particularly selected hook concentration or density (hooks per unit area). In a particular aspect, the hook density can be at least a minimum of about 1500 hooks/in$^2$ (about 232 hooks/cm$^2$). The hook density can alternatively be at least about 2000 hooks/in$^2$ (about 310 hooks/cm$^2$), and can optionally be at least about 3000 hooks/in$^2$ (about 465 hooks/cm$^2$) to provide improved performance. In another aspect, the hook density can be not more than a maximum of about 7000 hooks/in$^2$ (about 1085 hooks/cm$^2$). The hook density can alternatively be not more than about 6000 hooks/in$^2$ (about 930 hooks/cm$^2$), and can optionally be not more than about 5000 hooks/in$^2$ (about 775 hooks/cm$^2$) to provide improved performance.

Examples of suitable hook materials can include 85-Series and 61-Series hook materials available from Velcro, U.S.A., a business having offices located in Manchester, N.H., U.S.A. The hook materials can have a hook density of about 775 hooks/cm$^2$.

In a particular aspect, the material of the loop component 48 may include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. patent application Ser. No. 754,419 entitled PATTERN-UNBONDED NONWOVEN WEB AND PROCESS FOR MAKING THE SAME, by T. J. Stokes et al., and filed Dec. 17, 1996 (attorney docket No. 12,232), now U.S. Pat. No. 5,858,515 granted Jan. 12, 1999; the entire disclosure of which is incorporated herein by reference in a manner that is consistent herewith.

The complementary components of the mechanical fastener are configured to provide a selected attachment peel-force value. In a particular aspect, the peel-force value can be at least a minimum of about 75 grams (g). The peel-force value can alternatively be at least about 100 g, and can optionally be at least about 150 g to provide improved performance. In other aspects, the peel-force value can be up to a maximum of about 300 g, or more. The peel-force value can alternatively be up to about 250 g, and can optionally be up to about 225 g to provide improved effectiveness.

The complementary components of the mechanical fastener are also configured to provide a selected attachment shear-force value. In a particular aspect, the shear-force value can be at least a minimum of about 1000 g. The shear-force value can alternatively be at least about 1250 g, and can optionally be at least about 1500 g to provide improved performance. In other aspects, the shear-force value can be up to a maximum of about 3500 g, or more. The shear-force value can alternatively be up to about 3000 g, and can optionally be up to about 2000 g to provide improved effectiveness.

If the peel-force and/or the shear-force are outside the desired values, the fasteners may experience premature unfastening, or may be too difficult to unfasten to remove the article 20 from an associated undergarment.

In the construction of the article 20, the various components may be assembled and held together with any operative securement mechanism or system. For example, the desired attachments or securements can include adhesive bonds, cohesive bonds, thermal bonds, ultrasonic bonds, pins, snaps, staples, rivets, stitches, welds, zippers, or the like, as well as combinations thereof.

The following Examples describe particular configurations of the invention, and are presented to provide a more detailed understanding of the invention. The Examples are not intended to limit the scope of the present invention in any way. From a complete consideration of the entire disclosure, other arrangements within the scope of the claims will be readily apparent to one skilled in the art.

EXAMPLES

These Examples included a two layer absorbent system assembled between a cover and a baffle. The cover was composed of a 0.6 osy (about 20.3 g/m$^2$) spunbond nonwoven fabric with 0.45% AHCOVEL surfactant obtained from Uniqema, a business having offices located in New Castle, Del., U.S.A. The baffle was composed of a 1 mil, microembossed, polyethylene film obtained from Pliant Corporation, a business having offices located in Schaumburg, Ill., U.S.A.

The absorbent structure included an intake layer and an absorbent shaping layer. The intake layer can be selected from one of the configurations set forth in the following Table 1.

TABLE 1

| Intake Layer | A low basis weight and low density, homogeneous, stabilized, fibrous airlaid absorbent | Basis Wt. | Density |
| --- | --- | --- | --- |
| 1 | WEYERHAEUSER NF401 semi-treated woodpulp fluff fiber (90%); KoSa T255 bicomponent binder fiber (10%). | 120 g/m$^2$ | 0.06 g/cm$^3$ |
| 2 | WEYERHAEUSER NF401 semi-treated woodpulp fluff (90%); KoSa T255 bicomponent binder fiber (10%) | 175 g/m$^2$ | 0.06 g/cm$^3$ |

"semi-treated" means a debonding agent has been employed to treat the woodpulp fibers to improve opening and fiberization.
WEYERHAEUSER NF401 semi-treated fluff pulp is available from Weyerhaeuser, a business having offices located in Federal Way, Washington, U.S.A.
KoSa T255 bicomponent binder fiber is available from KoSA, a business having offices located in Houston, Texas, U.S.A.

The shaping layer can be selected from one of the configurations set forth in the following Table 1A.

TABLE 1A

| Shaping Layer | | | Basis Wt. | Density |
| --- | --- | --- | --- | --- |
| 1 | | A higher basis weight, higher density, stabilized, fibrous airlaid material; homogeneously blended fabric: | | |
| | A | 15% by weight STOCKHAUSEN FAVOR 9543 superabsorbent (SAP), 76.5% WEYERHAEUSER NB416 untreated woodpulp fluff fiber, and 8.5% KoSa T255 bicomponent binder fiber. | 175 g/m$^2$ | 0.12 g/cm$^3$ |
| | B | 15% by weight STOCKHAUSEN FAVOR 9543 SAP, 76.5% Weyerhaeuser NB416 untreated woodpulp fluff fiber, and 8.5% KoSa T255 bicomponent binder fiber | 225 g/m$^2$ | 0.12 g/cm$^3$ |
| 2 | | Integrally Layered, unitarily formed fabric. 15% by weight STOCKHAUSEN FAVOR 9543 SAP, 76.5% Weyerhaeuser NB416 untreated woodpulp fluff | 225 g/m$^2$ | 0.08 g/cm$^3$ overall |

TABLE 1A-continued

| Shaping Layer | | Basis Wt. | Density |
|---|---|---|---|
| | fiber, and 8.5% KoSa T255 bicomponent binder fiber. The bottom garment-side layer is compressed to approximately 0.12 g/cc, the middle layer is approximately 0.10 g/cc and the final compression of the material leaves the top bodyside layer at approximately 0.06 g/cc. Resulting in an overall target average of 0.08 g/cc. | | |
| 3 | A higher basis weight, higher density, compressed fluff material, layered fabric: | | |
| A | 83% by weight, Georgia Pacific 4800 untreated woodpulp fluff; 11% by weight Sumitomo Seika SA60s SAP layered in the middle of the fluff; and the garment side layer is 6% Duni KA-1810 tissue. | 318 g/m² | 0.12 g/cm³ |
| B | 79% by weight, Georgia Pacific 4800 untreated woodpulp fluff; 14% by weight Sumitomo Seika SA60s SAP and the garment side layer is 7% by weight Duni KA-1810 tissue. | 268 g/m² | 0.12 g/cm³ |

WEYERHAEUSER NB416 untreated woodpulp fluff is available from Weyerhaeuser, a business having offices located in Federal Way, Washington, U.S.A.
STOCKHAUSEN FAVOR 9543 superabsorbent polymer (SAP) and is available from Stockhausen GmbH & Co. KG, a business having offices located in Krefeld, Germany.
The "Integrally Layered, unitarily formed fabric" (shaping layer, sample 2) can be obtained from Concert Fabrication, a business having offices located in Gatineaux, Quebec, Canada.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. An absorbent feminine care article having a longitudinal direction, a lateral direction, first and second longitudinally opposed end portions, and an intermediate portion located between said end portions, said article comprising:
a liquid-permeable cover;
a baffle; and
an absorbent body sandwiched between the cover and baffle, said absorbent body including an intake layer and a shaping layer;
wherein
said shaping layer is positioned between said cover and said baffle;
said intake layer is positioned between said cover and said shaping layer;
said shaping layer includes therein a stabilized, thermally-bonded, airlaid, fibrous material having
bicomponent binder fiber,
at least about 5 wt % superabsorbent material, and
not more than about 75 wt % superabsorbent material;
said intake layer includes a stabilized, thermally-bonded, airlaid, fibrous material having bicomponent binder fiber therein;
said intake layer has a density which is less than a density of said shaping layer; and
said intake layer has an area extent which is less than an area extent of said shaping layer.

2. An article as recited in claim 1, wherein said absorbent body includes a transfer layer which is positioned between said intake layer and said pad shaping layer.

3. An article as recited in claim 1, wherein said shaping layer has a total absorbent saturation capacity of at least about 5 grams of menses simulant A.

4. An article as recited in claim 1, wherein said shaping layer has a total absorbent retention capacity of at least about 5 grams of menses simulant A.

5. An article as recited in claim 1, wherein said shaping layer has a basis weight of at least about 100 g/m² and not more than about 400 g/m².

6. An article as recited in claim 1, wherein said shaping layer has a density of at least about 0.06 g/cm³ and not more than about 0.3 g/cm³.

7. An article as recited in claim 1, wherein said intake layer has a total absorbent capacity which is less than a total absorbent capacity of said shaping layer.

8. An article as recited in claim 1, wherein said shaping layer includes a stabilized airlaid, fibrous material having woodpulp fluff and the bicomponent binder fiber therein.

9. An article as recited in claim 8, wherein said intake layer includes a stabilized airlaid, fibrous material having woodpulp fluff and the bicomponent binder fiber therein.

10. An absorbent feminine care article having a longitudinal direction, a lateral direction, first and second longitudinally opposed end portions, and an intermediate portion located between said end portions, said article comprising:
a liquid-permeable cover;
a baffle; and
an absorbent body sandwiched between the cover and baffle, said absorbent body including an intake layer and a shaping layer;
wherein
said shaping layer is positioned between said cover and said baffle;
said intake layer is positioned between said cover and said shaping layer;
said shaping layer has a shaping-layer basis weight of at least about 100 g/m² and not more than about 400 g/m², a shaping-layer density of at least about 0.06 g/cm³ and not more than about 0.3 g/cm³, a shaping-layer total absorbent saturation capacity of at least about 5 grams and not more than about 30 grams of menses simulant A, and a shaping-layer area of at least about 100 cm² and not more than about 150cm²;

said intake layer has an intake-layer density which is less than the shaping-layer density, is at least about 0.01 g/cm³, and is not more than about 0.1 g/cm³;

said intake layer has a basis weight of at least about 30 g/m² and not more than about 250 g/m²;

said intake layer has an intake-layer total absorbent capacity which is less than the shaping-layer total absorbent capacity, and has an intake-layer area which is less than the shaping-layer area;

said intake layer includes a first, stabilized, thermally-bonded, airlaid, fibrous material having woodpulp fluff and bicomponent binder fiber therein; and said shaping layer includes therein a second, stabilized, thermally-bonded, airlaid, fibrous material having woodpulp fluff and bicomponent binder fiber, at least about 5 wt % superabsorbent material, and not more man about 75 wt % superabsorbent material.

11. An article as recited in claim 10, wherein said intake layer has a lateral width which is at least about 25% of a lateral width of the shaping layer, and is up to about 85% of the lateral width of the shaping layer.

12. An article as recited in claim 11, wherein said intake layer has a longitudinal length which spans at least about 15% of a longitudinal length of the shaping layer, and up to about 90% of the longitudinal length of the shaping layer.

13. An article as recited in claim 10, wherein said intake layer has a lateral width which is at least about 25% of a lateral width of the shaping layer, and is up to about 75% of the lateral width of the shaping layer.

14. An article as recited in claim 13 wherein said intake layer has a longitudinal length which spans at least about 15% of a longitudinal length of the shaping layer, and up to about 90% of the longitudinal length of the shaping layer.

* * * * *